United States Patent
McAdams et al.

(10) Patent No.: US 9,014,988 B2
(45) Date of Patent: Apr. 21, 2015

(54) APPARATUS AND METHOD FOR DETERMINING MICROSCALE INTERACTIONS BASED ON COMPRESSIVE SENSORS SUCH AS CRYSTAL STRUCTURES

(75) Inventors: Harley McAdams, Stanford, CA (US); Mohammed AlQuraishi, Stanford, CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 247 days.

(21) Appl. No.: 13/426,824

(22) Filed: Mar. 22, 2012

(65) Prior Publication Data

US 2012/0244631 A1   Sep. 27, 2012

Related U.S. Application Data

(60) Provisional application No. 61/466,465, filed on Mar. 23, 2011.

(51) Int. Cl.
  *G06F 19/16* (2011.01)
  *G01N 23/20* (2006.01)
  *G06T 11/00* (2006.01)

(52) U.S. Cl.
  CPC ............... *G06F 19/16* (2013.01); *G01N 23/20* (2013.01); *G06T 11/006* (2013.01)

(58) Field of Classification Search
  CPC ... G21K 1/06; G01N 23/20; G01N 23/20008; C01P 2002/00; C01P 2002/04; C01P 2002/08; C01P 2002/70; C01P 2002/80
  See application file for complete search history.

(56) References Cited

U.S. PATENT DOCUMENTS

2009/0094012 A1* 4/2009 Clark ............................ 703/11
2009/0262996 A1* 10/2009 Samsonov et al. ............ 382/130

OTHER PUBLICATIONS

Robertson et al., An All-Atom, Distance-Dependent Scoring Function for the Prediction of Protein-DNA Interactions From Structure, Proteins: Structure, Function, and Bioinformatics 66:359-374, published online Oct. 31, 2006.*

Shental et al., Identification of rare alleles and their carriers using compressed se(que)nsing, Aug. 10, 2010, Nucleic Acids Research, vol. 38, No. 19, e179, pp. 1-22.*

V. E. Angarica, A. G. Perez, et al., "Prediction of TF target sites based on atomistic models of protein-DNA complexes", "BMC Bioinformatics", 2008, pp. 1-18, vol. 9, No. 436, Publisher: BioMed Central Ltd, Published in: www.biomedcentral.com/bmcbioinformatics/.

(Continued)

*Primary Examiner* — Melanie Yu Brown
*Assistant Examiner* — Rebecca Martinez
(74) *Attorney, Agent, or Firm* — Evans & Molinelli, PLLC; Eugene J. Molinelli

(57) ABSTRACT

Techniques for determining values for a metric of microscale interactions include determining a mesoscale metric for a plurality of mesoscale interaction types, wherein a value of the mesoscale metric for each mesoscale interaction type is based on a corresponding function of values of the microscale metric for the plurality of the microscale interaction types. A plurality of observations that indicate the values of the mesoscale metric are determined for the plurality of mesoscale interaction types. Values of the microscale metric are determined for the plurality of microscale interaction types based on the plurality of observations and the corresponding functions and compressed sensing.

15 Claims, 12 Drawing Sheets

(56) References Cited

OTHER PUBLICATIONS

E. J. Candes and J. Romberg, "Quantitative robust uncertainty principles and optimally sparse decompositions", "Foundations of Computational Mathematics", 2006, pp. 227-254, vol. 6, No. 2, Publisher: Springer, Published in: http://www.springer.com/mathematics/computational+science+%26+engineering/journal/10208.

E. Candes and T. Tao, "The Dantzig selector: Statistical estimation when p is much larger than n", "Annals of Statistics", 2007, pp. 2313-2351, vol. 35, No. 6, Publisher: Institute of Mathematical Statistics, Published in: http://projecteuclid.org/DPubS/Repository/1.0/Disseminate?handle=euclid.aos/1201012958&view=body&content-type=pdfview_1.

E. J. Candes and B. Recht, "Exact matrix completion via convex optimization", "Foundations of Computational Mathematics", 2008, pp. 717-772, vol. 9, Publisher: Springer, Published in: http://www.springer.com/mathematics/computational+science+%26+engineering/journal/10208.

E. Candes and Y. Plan, "A Probabilistic and RIPless Theory of Compressed Sensing", "IEEE Transactions on Information Theory", 2011, pp. 7235-7254, vol. 57, No. 11, Publisher: IEEE, Published in: http://ieeexplore.ieee.org/xpl/tocresult.jsp?isnumber=6071748&punumber=18.

J. E. Donald, W. W. Chen, et al., "Energetics of protein-DNA interactions", "Nucleic Acids Research", 2007, pp. 1039-1047, vol. 35, No. 4, Publisher: Oxford University Press, Published in: http://nar.oxfordjournals.org/content/35/4/1039.full.pdf+html.

J. Friedman, T. Hastie, et al., "Regularization Paths for Generalized Linear Models via Coordinate Descent", "Journal of Statistical Software", 2010, pp. 1-22, vol. 33, No. 1, Publisher: American Statistical Association, Published in: http://www.jstatsoft.org/v33/i01.

G. M. James and P. Radchenko, "A generalized Dantzig selector with shrinkage tuning", "Biometrika", 2009, pp. 323-337, vol. 96, No. 2, Publisher: Biometrika Trust, Published in: http://biomet.oxfordjournals.org/content/96/2/323.full.pdf+html.

A. V. Morozov, J. J. Havranek, et al., "Protein-DNA binding specificity predictions with structural models","Nucleic Acids Research", 2005, pp. 5781-5798, vol. 33, No. 18, Publisher: Oxford University Press, Published in: http://nar.oxfordjournals.org/content/33/18/5781.full.pdf+html.

A. V. Morozov and E. D. Siggia, "Connecting protein structure with predictions of regulatory sites", "Proceedings of the National Academy of Sciences", 2007, pp. 7068-7073, vol. 104, No. 17, Publisher: National Academy of Sciences, Published in: http://www.pnas.org/content/104/17/7068.full.pdf+html.

R. Tibshirani, "Regression shrinkage and selection via the Lasso", "Journal of the Royal Statistical Society, Series B (Methodological)", 1996, pp. 267-288, vol. 58, No. 1, Publisher: Royal Statistical Society, Published in: http://links:jstor.org/sici?sici=0035-9246%281996%2958%3A1%3C267%ARSASVT%E2.0.CO%3B2-G.

J. A. Tropp, "On the conditioning of random subdictionaries", "Applied and Computational Harmonic Analysis", 2008, pp. 1-24, vol. 25, No. 1, Publisher: Elsevier, Published in: Amsterdam.

* cited by examiner

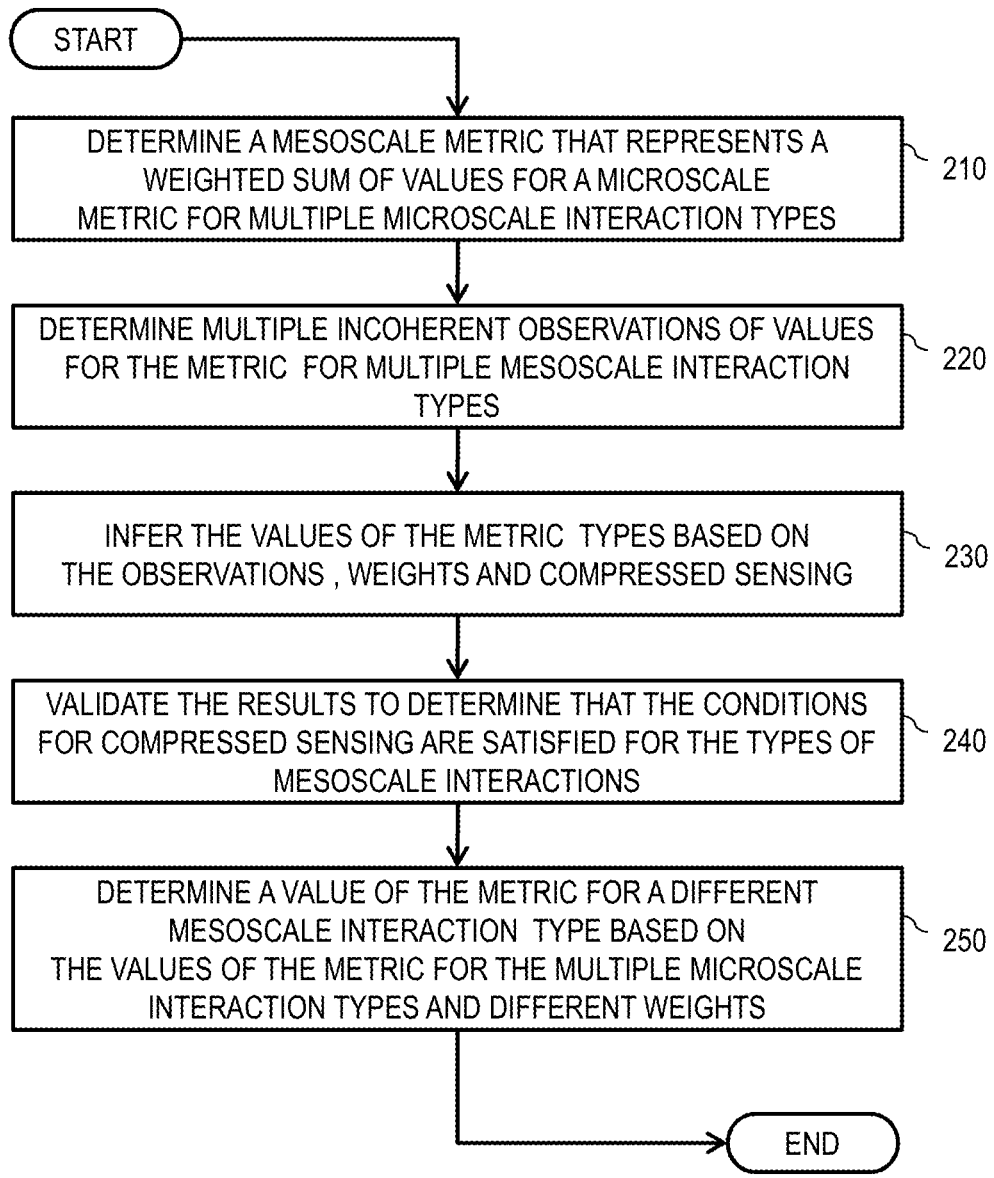

FIG. 6A

| SEQ ID NO | | | SEQ ID NO |
|---|---|---|---|
| 14 | CGCCATAAAT | 601 CATGTAAAA | 15 |
| 16 | CGCCATAAAT | 603 CATGTAAAA | 17 |
| 18 | CCCTACACGC | 605 GCTTGCCCG | 19 |
| 20 | GTCAATTAAC | 607 CTTTAATTG | 21 |
| 22 | GGGGATGGTC | 609 GGGGGGAGGG | 23 |

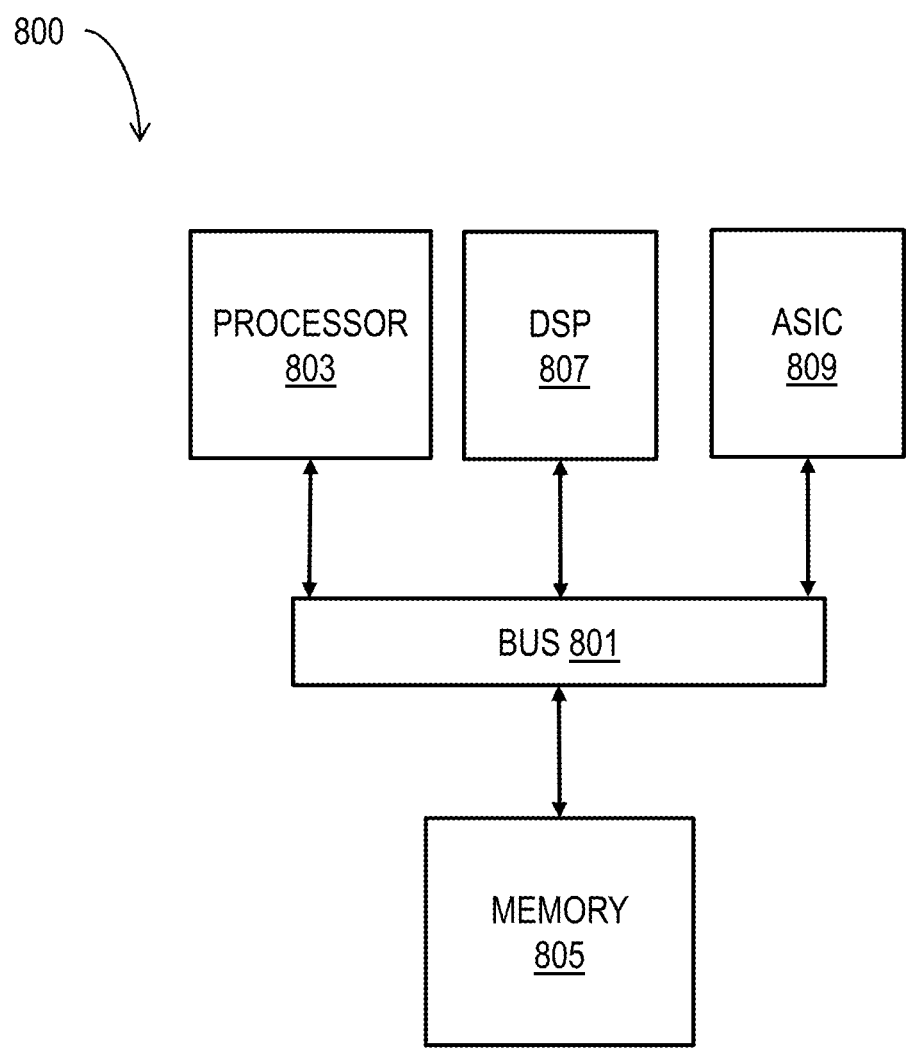

```
                        SEQUENCE LISTING

<160> NUMBER OF SEQ ID NOS: 30

<210> SEQ ID NO 1
   <211> LENGTH: 10
   <212> TYPE: DNA
   <213> ORGANISM: Artificial Sequence
   <220> FEATURE:
   <223> OTHER INFORMATION: Synthetic

<400> SEQUENCE: 1
aaaatgcgat                                                                 10

<210> SEQ ID NO 2
   <211> LENGTH: 10
   <212> TYPE: DNA
   <213> ORGANISM: Artificial Sequence
   <220> FEATURE:
   <223> OTHER INFORMATION: Synthetic

<400> SEQUENCE: 2
aaaatgcgat                                                                 10

<210> SEQ ID NO 3
   <211> LENGTH: 9
   <212> TYPE: DNA
   <213> ORGANISM: Artificial Sequence
   <220> FEATURE:
   <223> OTHER INFORMATION: Synthetic

<400> SEQUENCE: 3 ctatcaccg                                                                   9

<210> SEQ ID NO 4
   <211> LENGTH: 9
   <212> TYPE: DNA
   <213> ORGANISM: Artificial Sequence
   <220> FEATURE:
   <223> OTHER INFORMATION: Synthetic

<400> SEQUENCE: 4 gtatcaccg                                                                   9

<210> SEQ ID NO 5
   <211> LENGTH: 13
   <212> TYPE: DNA
   <213> ORGANISM: Artificial Sequence
   <220> FEATURE:
   <223> OTHER INFORMATION: Synthetic
```

-continued

```
<400> SEQUENCE: 5
gccggagatg ggc                                                          13

<210> SEQ ID NO 6
<211> LENGTH: 13
<212> TYPE: DNA
<213> ORGANISM: Artificial Sequence
<220> FEATURE:
<223> OTHER INFORMATION: Synthetic

<400> SEQUENCE: 6
cggggagatg ggg                                                          13

<210> SEQ ID NO 7
<211> LENGTH: 7
<212> TYPE: DNA
<213> ORGANISM: Artificial Sequence
<220> FEATURE:
<223> OTHER INFORMATION: Synthetic

<400> SEQUENCE: 7 ttcacgc                                                                  7

<210> SEQ ID NO 8
<211> LENGTH: 8
<212> TYPE: DNA
<213> ORGANISM: Artificial Sequence
<220> FEATURE:
<223> OTHER INFORMATION: Synthetic

<400> SEQUENCE: 8 cttcacgc                                                                 8

<210> SEQ ID NO 9
<211> LENGTH: 12
<212> TYPE: DNA
<213> ORGANISM: Artificial Sequence
<220> FEATURE:
<223> OTHER INFORMATION: Synthetic

<400> SEQUENCE: 9
aaaagaggaa gt                                                           12

<210> SEQ ID NO 10
<211> LENGTH: 9
<212> TYPE: DNA
<213> ORGANISM: Artificial Sequence
<220> FEATURE:
<223> OTHER INFORMATION: Synthetic

<400> SEQUENCE: 10 accggaagt                                                                9

<210> SEQ ID NO 11
<211> LENGTH: 13
<212> TYPE: DNA
<213> ORGANISM: Artificial Sequence
<220> FEATURE:
<223> OTHER INFORMATION: Synthetic

<400> SEQUENCE: 11
agccgctcac aac                                                          13

<210> SEQ ID NO 12
```

```
<211> LENGTH: 13
<212> TYPE: DNA
<213> ORGANISM: Artificial Sequence
<220> FEATURE:
<223> OTHER INFORMATION: Synthetic

<400> SEQUENCE: 12
ttggagaagt tgt                                                          13

<210> SEQ ID NO 13
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 13
aanngntnac a                                                            11

<210> SEQ ID NO 14
<211> LENGTH: 10
<212> TYPE: DNA
<213> ORGANISM: Artificial Sequence
<220> FEATURE:
<223> OTHER INFORMATION: Synthetic

<400> SEQUENCE: 14
cgccataaat                                                              10

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15 catgtaaaa                                                                9

<210> SEQ ID NO 16
<211> LENGTH: 10
<212> TYPE: DNA
<213> ORGANISM: Artificial Sequence
<220> FEATURE:
<223> OTHER INFORMATION: Synthetic

<400> SEQUENCE: 16
cgccataaat                                                              10

<210> SEQ ID NO 17
<211> LENGTH: 9
<212> TYPE: DNA
<213> ORGANISM: Artificial Sequence
<220> FEATURE:
<223> OTHER INFORMATION: Synthetic

<400> SEQUENCE: 17
```

```
catgtaaaa                                                                9

<210> SEQ ID NO 18
<211> LENGTH: 10
<212> TYPE: DNA
<213> ORGANISM: Artificial Sequence
<220> FEATURE:
<223> OTHER INFORMATION: Synthetic

<400> SEQUENCE: 18
ccctacacgc                                                              10

<210> SEQ ID NO 19
<211> LENGTH: 9
<212> TYPE: DNA
<213> ORGANISM: Artificial Sequence
<220> FEATURE:
<223> OTHER INFORMATION: Synthetic

<400> SEQUENCE: 19 gcttgcccg                                                                9

<210> SEQ ID NO 20
<211> LENGTH: 10
<212> TYPE: DNA
<213> ORGANISM: Artificial Sequence
<220> FEATURE:
<223> OTHER INFORMATION: Synthetic

<400> SEQUENCE: 20
gtcaattaac                                                              10

<210> SEQ ID NO 21
<211> LENGTH: 9
<212> TYPE: DNA
<213> ORGANISM: Artificial Sequence
<220> FEATURE:
<223> OTHER INFORMATION: Synthetic

<400> SEQUENCE: 21 ctttaattg                                                                9

<210> SEQ ID NO 22
<211> LENGTH: 10
<212> TYPE: DNA
<213> ORGANISM: Artificial Sequence
<220> FEATURE:
<223> OTHER INFORMATION: Synthetic

<400> SEQUENCE: 22
ggggatggtc                                                              10

<210> SEQ ID NO 23
<211> LENGTH: 9
<212> TYPE: DNA
<213> ORGANISM: Artificial Sequence
<220> FEATURE:
<223> OTHER INFORMATION: Synthetic

<400> SEQUENCE: 23 gggggaggg                                                                9

<210> SEQ ID NO 24
<211> LENGTH: 7
<212> TYPE: DNA
```

```
<213> ORGANISM: Artificial Sequence
<220> FEATURE:
<223> OTHER INFORMATION: Synthetic

<400> SEQUENCE: 24 ttcacgc                                                                     7

<210> SEQ ID NO 25
<211> LENGTH: 6
<212> TYPE: DNA
<213> ORGANISM: Artificial Sequence
<220> FEATURE:
<223> OTHER INFORMATION: Synthetic

<400> SEQUENCE: 25 taatta                                                                      6

<210> SEQ ID NO 26
<211> LENGTH: 8
<212> TYPE: DNA
<213> ORGANISM: Artificial Sequence
<220> FEATURE:
<223> OTHER INFORMATION: Synthetic

<400> SEQUENCE: 26 cttcacgc                                                                    8

<210> SEQ ID NO 27
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 27 naattaa                                                                     7

<210> SEQ ID NO 28
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 28 tttnanaa                                                                    8

<210> SEQ ID NO 29
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
```

```
<220> FEATURE:
<221> NAME/KEY: misc_feature
<222> LOCATION: (3)..(3)
<223> OTHER INFORMATION: n is a, c, g, or t

<400> SEQUENCE: 29 ntnatca                                                                     7

<210> SEQ ID NO 30
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 30 ttntnan                                                                     7
```

APPARATUS AND METHOD FOR DETERMINING MICROSCALE INTERACTIONS BASED ON COMPRESSIVE SENSORS SUCH AS CRYSTAL STRUCTURES

CROSS-REFERENCE TO RELATED APPLICATIONS

This application claims benefit of Provisional Appln. 61/466,465, filed Mar. 23, 2011, the entire contents of which are hereby incorporated by reference as if fully set forth herein, under 35 U.S.C. §119(e).

STATEMENT OF GOVERNMENTAL INTEREST

This invention was made with Government support under Grant No. DE-FG02-05ER64136 awarded by the Office of Science of the Department of the Energy. The Government has certain rights in the invention.

BACKGROUND OF THE INVENTION

The determination of microscale interaction energies (also called potentials herein) during binding or folding of large molecules, such as proteins and nucleic acids, has been limited by the experimental difficulty of directly measuring atomic-scale interactions within such large molecules. Furthermore the number of interactions involved is very large, as each atom type in one molecule can possibly interact with each atom type in itself (for folding) or the other molecule (for binding). The interaction is often distance dependent, further increasing the number of interactions for which interaction energies are to be determined. For example, if it is assumed that a dozen atom types in one molecule can interact with each of twenty atom types in another molecule at each of 15 different distances, then the number of interaction energies to determine is 3,600. In general, the combinatorially large number of measurements required to comprehensively characterize the potential that describes all possible microscale interactions in a molecular system is at least daunting and expensive, if not prohibitive. As a result of this experimental intractability, interaction energies to date have relied on theoretical models.

SUMMARY OF THE INVENTION

Therefore, there is a need for an approach for determining values for a microscale interaction metric, such as interaction energy, which does not suffer one or more of the disadvantages of prior approaches, such as relying on theoretical models or numerous a priori assumptions. Techniques are provided for determining, based on compressive sensing, values for a metric of microscale interactions beyond direct observation. In various embodiments, the compressive sensors are mesoscale interactions for which a corresponding metric is a function of values for the metric of some or all of the microscale interactions. In several embodiments, the compressive sensors are crystal structures.

In a first set of embodiments, a method includes determining a microscale metric for multiple microscale interaction types and determining a mesoscale metric for multiple mesoscale interaction types. A value of the mesoscale metric for each mesoscale interaction type is based on a corresponding function of values of the microscale metric for the microscale interaction types. A plurality of observations that indicate the values of the mesoscale metric are obtained for the mesoscale interaction types. Values of the microscale metric for the microscale interaction types are determined based on the observations and the corresponding functions and compressed sensing.

In some embodiments of the first set, the microscale interactions include sub-molecular interactions involving a plurality of atoms or atom complexes.

In some embodiments of the first set, the mesoscale interactions include molecular interactions involving at least one large molecule.

In some embodiments of the first set, each of the plurality of observations comprises relative rate of occurrence of the mesoscale interactions in a canonical ensemble.

In some embodiments of the first set, the metric of the mesoscale interaction is binding energy or folding energy.

In some embodiments of the first set, a majority of values of the metric for the plurality of microscale interactions are negligible.

In other sets of embodiments, a computer readable medium or an apparatus is configured to perform one or more steps of the above methods.

Still other aspects, features, and advantages of the invention are readily apparent from the following detailed description simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A is flowchart that illustrates an example method for determining and using values of a microscale interaction metric from values of a mesoscale interaction metric, according to one embodiment;

FIG. 8 illustrates a chip set upon which an embodiment of the invention may be implemented.

DETAILED DESCRIPTION

Figure 1:
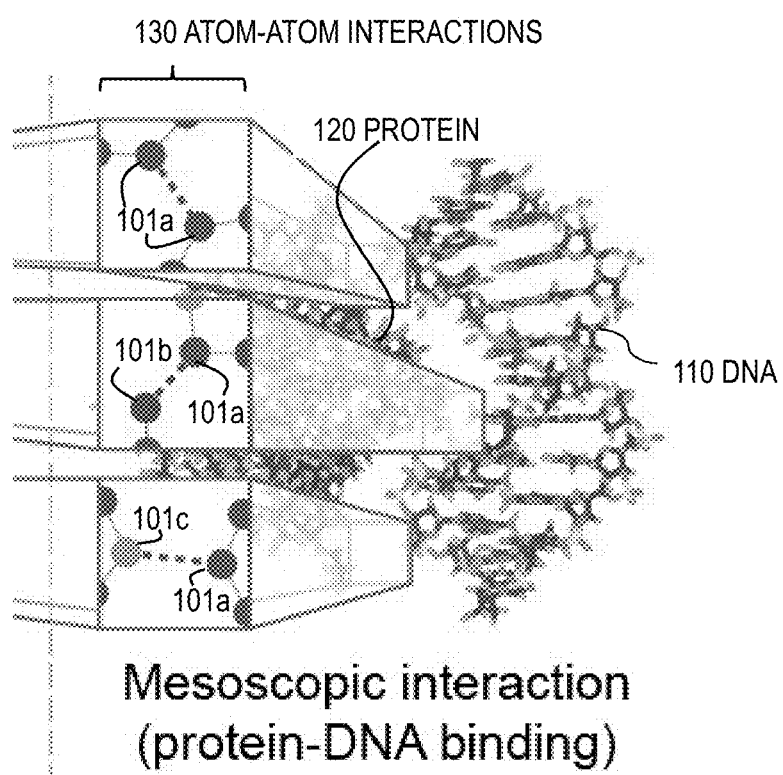
FIG. 1, is a block diagram that illustrates example protein DNA binding (PDB) involving a small subset of atomic interactions.

A method and apparatus are described for determining values of a metric of microscale interactions based on compressive sensors. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. Various references are cited in the following. The entire contents of the following references are hereby incorporated by reference as if fully set forth herein, except for terminology that is inconsistent with the terminology used herein. As used herein, the following terms and abbreviations have the meanings given in Table. 1.

TABLE 1

| Terms and Definitions. | |
|---|---|
| alpha helix (α-helix) | A right-handed coiled or spiral conformation of a protein, in which every backbone Nitrogen-Hydrogen (N—H) group donates a hydrogen bond to the backbone Carbon Oxygen double bond (C=O) group of the amino acid four residues earlier (i.e., hydrogen bonding). Among types of local structure in proteins, the α-helix is the most regular and the most predictable form sequence, as well as the most prevalent. |
| canonical ensemble | A set of physical states in which the mesoscale interaction energy may vary, but the volume, temperature, and number of particles are fixed |
| consensus sequence | A sequence of DNA nucleotides (bases) where a particular protein is most likely to bind to a DNA helix, as found by experiment. |
| CS | Compressed sensing - known technique for deriving a signal (e.g., an image) from compressed measurements (e.g., summed intensities of pixels). |
| De novo | A shorthand reference for the new compressed sensing approach presented herein for deriving values of microscale interaction energy to distinguish this approach from physical and statistical derivations. |
| DNA | Deoxyribonucleic acid - a double helix comprising two complementary sequences of nucleotide bases (each selected from a set of four nucleotides: adenine, thymine, cytosine, and guanine, represented by the letters A, T, C and G, respectively) |
| energy profile, V(r, q) | a mathematical description of the interaction energy V at a distance r of each possible interaction q in a molecular system, where q is an index that indicates a particular interacting set of two or more atoms. |
| HTH | Helix-turn-helix proteins composed of two α helices joined by a short strand of amino acids and found in many proteins that regulate gene expression. |
| $l_1$ norm | A size of vectors given by the sum of absolute values of vector elements. |
| mesoscale | Spatial scales on the same order as the resolution of available observations, also called mesoscopic. |
| mesoscale interaction | Also called mesoscopic interaction, an interaction for which a metric is a function of the values of a metric of its constituent microscale interactions |
| microscale | Spatial scales smaller than the resolution of available observations, also called microscopic. |
| microscale interaction | Also called microscopic interaction, an interaction on the microscale. |
| parameter | A term in an equation that is constant for a particular application or context, but can vary among different applications or contexts. |
| potential | In context of a microscale metric, the microscale interaction energy. |
| position weight matrix (PWM) | A matrix of probabilities that gives a weighted match to any given substring of fixed length. It has one row for each symbol of the alphabet, and one column for each position in the substring. The match at a particular row and column is the probability that the symbol of the row appears at the position of the column. The probability for a string of symbols is the product of position-specific probabilities for each symbol in the substring. A PWM is commonly used as a representation of motifs (patterns) in biological sequences with an alphabet of 4 nucleotide bases. A PWM is also called position-specific weight matrix (PSWM) or position-specific scoring matrix (PSSM) where probabilities are replaced by the general notion of likelihood. |
| PDB | Protein Data Bank |
| Protein-DNA binding structure | A complex formed by binding forces between a section of DNA and one or more parts of a protein molecule. |
| RNA | Ribonucleic acid - a single sequence of nucleotide bases (each selected from a set of four nucleotides: adenine, uracil, cytosine, and guanine, represented by the letters A, U, C and G. |

TABLE 1-continued

Terms and Definitions.

| | |
|---|---|
| Symmetric Kullback-Leibler divergence (SKLD) metric | A symmetric and non-negative measure of the difference between two probability distributions P and Q based on an average of the logarithmic difference between the probabilities P and Q. Typically P represents the "true" distribution of data, observations, or a precise calculated theoretical distribution. The measure Q typically represents a theory, model, description, or approximation of P. |
| variable | A term in an equation that can assume multiple different values for a single application or context. |

Some embodiments of the invention are described below in the context of binding energy of mesoscale protein-DNA binding and values of potential of microscale atom-atom interactions. However, the invention is not limited to this context. In other embodiments microscale interaction energies are determined for protein-protein binding and protein folding and other molecular binding or folding interactions. In some embodiments, other metrics of microscale interactions are determined, such as kinetic metrics, including residence binding efficiency and residence times. In some embodiments, the microscale interactions are not atomic interactions. For example, in some embodiments, a microscale interaction is an interaction among multiple atoms on each of the two interacting molecules. In some embodiments, a microscale interaction is a complex system of multiple molecules in conjunction with a solvent or crystal.

In some embodiments, the same elements interacting at different distances are treated as different interactions rather than a distance-dependent interaction of those elements. In some embodiments, an interaction depends on the chemical environment of the interacting elements, in which case the same elements interacting in different chemical environments, e.g., at different locations along a long molecule, correspond to different interactions.

1. Overview

FIG. 1 is a block diagram that illustrates example protein DNA binding involving a small subset of atomic interactions. The DNA molecule 110 binds to the protein molecule 120 through multiple atom-atom interactions 130. For example atom type 101a on the protein molecule 120 binds to an atom of the same type 101a on the DNA molecule 110. In addition, atom type 101b on the protein molecule 120 binds to an atom of the type 101a on the DNA molecule 110; and atom type 101c on the protein molecule 120 binds to an atom of the type 101a on the DNA molecule 110. Other atom-atom interactions are not shown. In some embodiments, the binding energy of the protein molecule 120 and DNA molecule 110 are known from biochemical measurements. However, the potentials of the atom-atom interactions are desired for a variety of purposes, including predicting the relative strengths of other protein-DNA bindings.

In the illustrated context, the binding of the protein-DNA complex captured in a crystal structure is the mesoscale interaction, and the atom-atom interactions are the microscale interactions. The binding energy is enough to form the compound that is crystallized. Furthermore crystal studies (e.g., x-ray crystallography) indicate the position and orientation of atoms in the region of binding so that the functional dependence of each mesoscale interaction type on each microscale interaction type is known, or approximated. In other embodiments, other techniques (e.g., nuclear magnetic resonance, cryo-electron microscopy or atomic force microscopy) are used to determine the microscale interaction types in each mesoscale interaction type and thus the corresponding function for each mesoscale interaction type. It is recognized here that of all the possible atom-atom interactions, only a limited number are non-negligible for protein-DNA binding. That is, the solution matrix is sparse. For example, atoms of type 101b on DNA molecule 110 do not interact with atoms of type 101b on protein molecule 120. This realization allows one to use the methods of compressed sensing.

Thus, according to some embodiments, by examining the binding energies or relative occurrences of interactions of several different protein-DNA complexes, e.g., in corresponding different crystals, and using the linear regression methods of compressed sensing, the atom-atom interaction energies can be inferred.

The method involves a novel mathematical formulation that recasts the determination of potentials at the microscale, for example, as a signal acquisition problem using compressed sensing techniques. By exploiting a key property of compressed sensing (discussed below), the experimental intractability of determining potentials, for example, is circumvented. This formulation rests on three key observations. (i) In certain systems, e.g. biomolecular interactions, only a few types of inter-atomic interactions, such as hydrogen bonds, are energetically important. (ii) Mesoscale interactions, e.g. protein-DNA binding, can be viewed as sensors of (and, thus, somewhat known functions of) the underlying microscale potential. (iii) In embodiments that target potentials, there is a correspondence between the mathematical formulation of logistic regression and the statistical mechanical concept of the canonical ensemble.

Using these ideas, the determination of potentials is formulated as a tractable signal acquisition problem as described in a later section. Central to this approach is the distinction between microscale and mesoscale interactions. An important characteristic is that mesoscale interactions be comprised of microscale interactions, such that a value of the metric (e.g., binding energy) of a mesoscale interaction is a function of the values of the metric (e.g., potential) of its constituent microscale interactions. The function that identifies or approximates or otherwise indicates the microscale interactions constituting each mesoscale interaction must also be known or approximated. Some embodiments include determining for each mesoscale interaction type the corresponding function of values of the microscale metric for the plurality of the microscale interaction types. In various embodiments, for each mesoscale interaction the corresponding function is determined based on measurements from a member of a group comprising x-ray crystallography, nuclear magnetic resonance, cryo-electron microscopy, and atomic force microscopy, or equivalents thereof. In the illustrated embodiments, the term "mesoscale interactions" refers to interactions between molecules or molecular complexes, while "microscale interactions" refers to interactions at the atomic scale. This distinction is ultimately application-specific, and depends on what interaction metrics are to be determined and what experimental data is available.

When these requirements are met substantively, the method can determine the values of the metric (e.g., potential) of the microscale interactions using observations that indicate the values of the metric (e.g., binding energy or probability of the mesoscale interactions) as the experimental data. For protein-DNA interactions, the mesoscale interactions are protein-nucleotide binding events represented by protein-DNA crystal structures with known binding energies or relative binding probabilities, and the microscale interactions are pairwise, distance-dependent, contacts between protein atoms and nucleotide atoms (standard atom type categories are used and distances are segmented into discrete bins whose widths are treated as model parameters as described below).

Thus, each protein-nucleotide crystal structure characterizes a mesoscale interaction whose constituent microscale interactions are readily identified from the structure. In some embodiments, intra-protein and intra-DNA energies are ignored because approximations of the protein-DNA interactions are the focus. These data are used together with the known energies or probabilities of protein-nucleotide binding events to infer de novo the inter-atomic protein-DNA potentials. In the following, the compressed sensing determination of the values of the microscale metric according to the illustrated embodiments, are called de novo to distinguish from purely physical or purely statistical approaches, and the resulting potentials are called de novo potentials. In further steps, it is shown that these de novo potentials can be used to predict protein-DNA binding motifs with unprecedented accuracy.

FIG. 2A is flowchart that illustrates an example method for determining values of a metric for multiple microscale interaction types from observations of a metric for mesoscale interaction types, according to one embodiment. In step 210 a mesoscale interaction metric (called a mesoscale metric, hereinafter) is determined that represents a function of values of a corresponding metric (called a microscale metric, hereinafter) for multiple microscale interaction types.

For example, as depicted in FIG. 1, it is determined that protein-DNA binding in crystals is a type of meso scale interaction for which the mesoscale metric is binding energy that represents a weighted sum of values for potential (microscale metric) for multiple atom-atom microscale interaction types. More details on this relationship are described in subsequent sections. Observations of values for the mesoscale metric, e.g. protein-DNA binding energy, can be direct or can be indirect, e.g., deduced from relative rate of occurrence in a crystal comprising many instances of the same protein molecule bound to the same DNA molecule. From these observations and knowledge of the function (e.g., weights) for the microscale interactions, and compressed sensing methods, the values of the microscale metric (e.g., potential) can be derived for the non-negligible microscale interaction types (e.g., particular atom pairs)

Figure 2B:
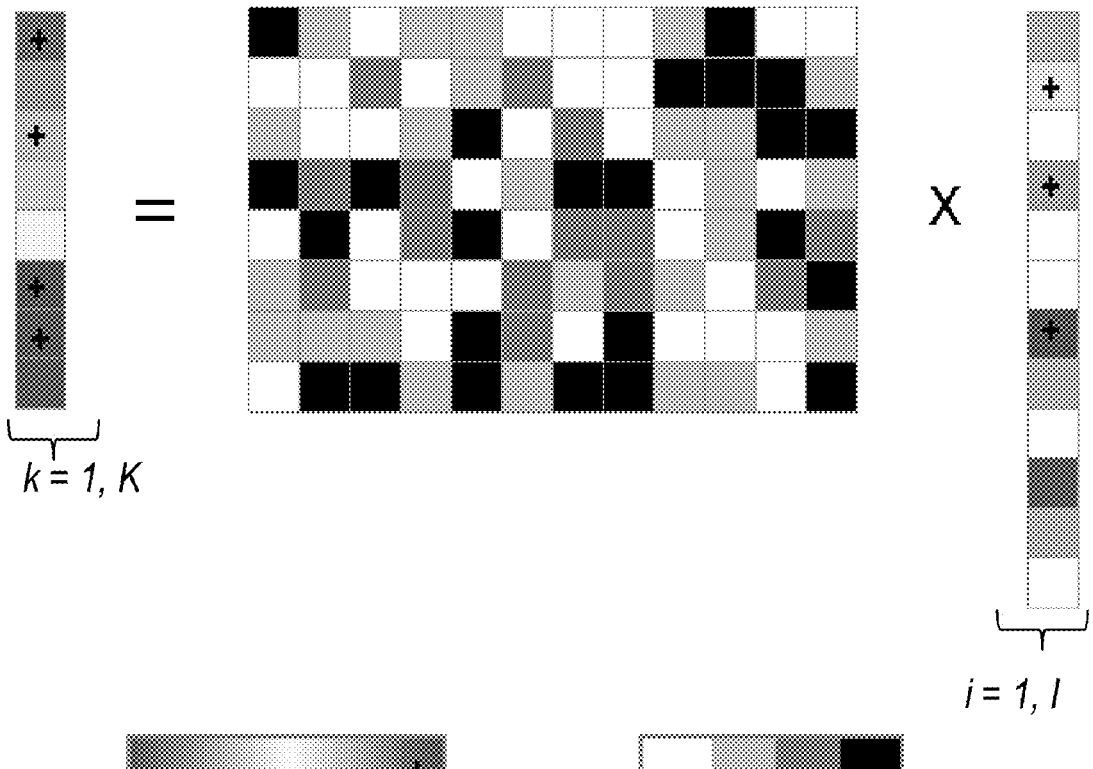
FIG. 2B is a block diagram that illustrates an example compressed sampling relationship between values of a metric of mesoscale interactions and values of a metric for microscale interactions, according to an embodiment.

FIG. 2B is a block diagram that illustrates an example compressed sampling relationship C 270 between values of a metric of mesoscale interactions E 274 and values of a metric of microscale interactions e 272, according to an embodiment. The value of the metric is given by the energy scale 262, with larger energies indicated by plus sign. The value in each element of the function (or weighted sum) matrix C is given by the interaction count scale bar 264, with darker indicating a greater count (or weight of a weighted sum). In compressed sensing, the objective is to infer an unknown signal, represented by the vector e 272 with elements $e_i$, i=1, I, from a set of measurements represented by the vector E 274 with elements $E_k$, k=1, K. The relationship between the measurements and the signal is assumed to satisfy the function given by the equation E=C×e; i.e., each measurement $E_k$ is formed by the inner product of the kth row of C 270 with the vector e, e.g., a weighted sum of the values of e, where the elements in C provide the weights. C has K rows and each row of C has I values, and an arbitrary element in C is designated $C_{ik}$. Thus each row of C represents a distinct sensor vector, embodied in a particular type of mesoscale interaction. The number of measurements available (i.e., K the length of E) is typically much smaller than the length of the signal vector e, which would make the equation E=C×e impossible to solve in general. However, for a sparse signal vector e, with many negligible values $e_i$, compressed sensing techniques enable inference of the original signal e.

In the protein-DNA embodiment illustrated below, the signal e is the vector of microscale interaction energies (protein-DNA atomic potential), where each entry $e_i$ in the signal vector e corresponds to the energy of an interaction between a protein atom type and a DNA atom type within a discrete distance bin. Thus the energy profile V(r,q) for multiple radii r and atom sets q is represented by the $e_i$ for all i. Each row of C arises from a distinct protein-DNA crystal structure, and each column corresponds to a distinct type of microscale interaction (combination of protein atom type, DNA atom type, and distance bin). An element $C_{ik}$ of C encodes the number of times (indicated by gray levels 264) that the ith interaction type occurs in the kth crystal structure. The set of measurements $E_k$ are the experimental direct or relative binding energies of the corresponding protein-DNA complexes. Because the binding energy of a complex is the sum of the energies of all microscale interactions in the complex, it is equal to the weighted sum given by the inner product between the kth row of C that encodes the kth complex and the signal vector e.

In other embodiments, other microscale interaction types, microscale metrics, mesoscale interaction types, mesoscale metrics and observations are utilized. In some other embodiments, the energy measurements are of the folding energies of one or more proteins or other large molecules. Energy of mesoscale interactions is used herein to refer to either binding or folding energies of mesoscale interactions, or some combination. For example, in various embodiments, mesoscale interactions include protein folding, enzyme-substrate affinities, RNA-DNA interactions, RNA-protein interactions, RNA-RNA interactions, DNA-DNA interactions, protein-protein binding energies, DNA and protein-small molecule affinities, liquid-solid surface interactions, solid surface-solid surface interactions, crystal-crystal interactions, interactions including two, three, or a multiplicity of atoms, interactions involving sets of defined atoms (e.g., residue with base), interactions involving atoms with mesoscale objects such as a solvent, organic molecule or inorganic molecule interactions, or a mixture of organic and inorganic molecules. If the energy of the mesoscale interaction can be obtained, and an atomic resolution structure involved in the mesoscale interaction can also be obtained, then regardless of the type of molecules involved, the method is applicable. The accuracy achieved depends on the sparsity of the underlying microscale interactions, but with sufficient data, even dense microscale interactions can be inferred. In various embodiments, mesoscale metrics include a direct energy or relative energy for binding energy or for folding energy.

Figure 3A:
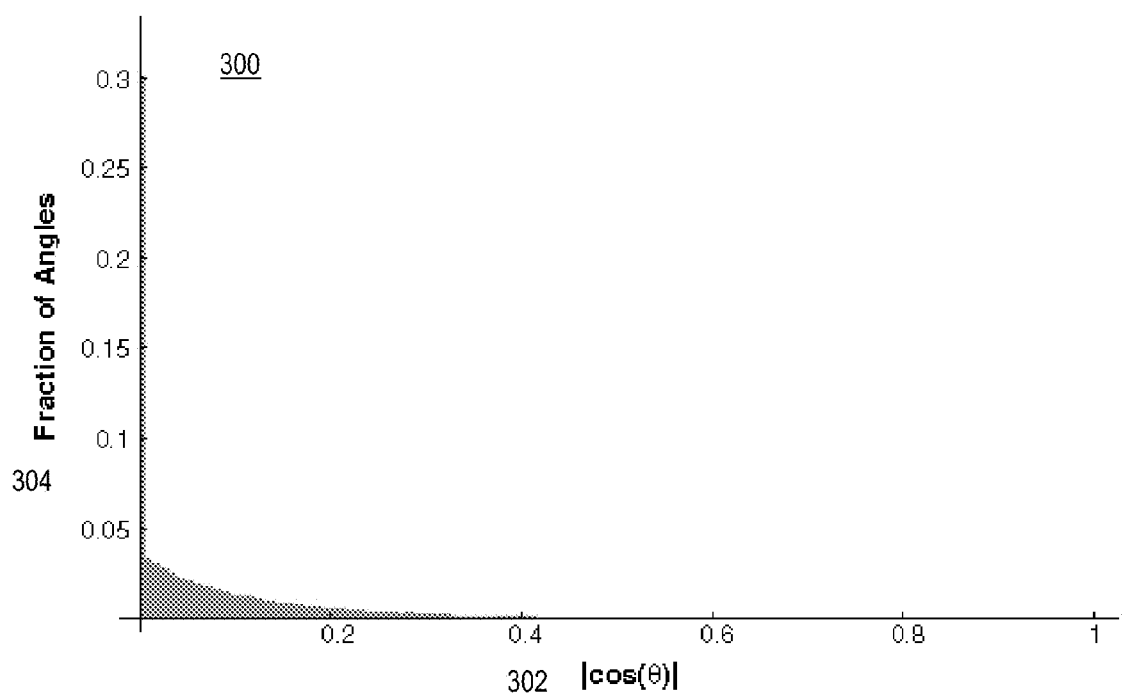
FIG. 3A is a graph that illustrates example measure of incoherence of measurements, according to an embodiment.

Returning to FIG. 2A, in step 220, multiple incoherent observations of values for the metric of different types of mesoscale interactions are obtained. "Incoherence" is a term used in compressed sensing literature that relates to the randomness of the set of microscale interactions sampled by the mesoscale sensor. For example, physical measurements are made of the binding energies or relative occurrence rates for several different DNA sequences and the same protein in a corresponding set of different crystals. FIG. 3A is a graph 300 that illustrates example measure of incoherence of measurements, according to an embodiment. The horizontal axis 302 indicates the cosine of the angle between any two rows of the matrix C, called sensor vectors, and is dimensionless. The vertical axis 304 indicates the fraction of the total number of pairs that have that angle and, is also dimensionless. For every pair of sensor vectors derived from the dataset and used in the best performing "Baseline" model described below, the cos θ values are as shown. This distribution characterizes the incoherence of the sensor matrix used. For an effective sensor matrix, it is desirable to have as many of the values be close to 0 as possible. The observed distribution suggests that the dataset used can act as an effective sensor matrix, with mean and median values of 0.081 and 0.041 (in units of j cos θj), respectively. These values are significantly lower than 1, thus indicating that the set of sensors comprised by the protein:DNA crystal structures in the illustrated data set has good incoherence properties.

In some embodiments, obtaining the observations includes entering or retrieving data of previously made measurements, such as published observations. In some embodiments, obtaining the observations includes calculating the energies from partial data and accepted mathematical derivation, e.g., computing binding energies of DNA sequences with at least one different base in at least one position of the sequence, based on measurements of a single protein binding for a single DNA sequence. More details on obtaining observations are provided in subsequent sections.

Returning to FIG. 2A, in step 230 values for the metric for the multiple microscale interaction types are inferred based on the observations and the methods of compressed sensing. This process is described in detail in a subsequent section where the microscale metric is interaction energy (potential). Accuracy of this step relies on the degree to which the system selected in step 210 satisfies the conditions for compressed sensing, e.g., a sparse solution set with a majority of microscale interactions that have metric values that are negligible. Step 230 includes determining reasonable values for one or more compressive sensing parameters, e.g., based on training data.

Figure 3B:
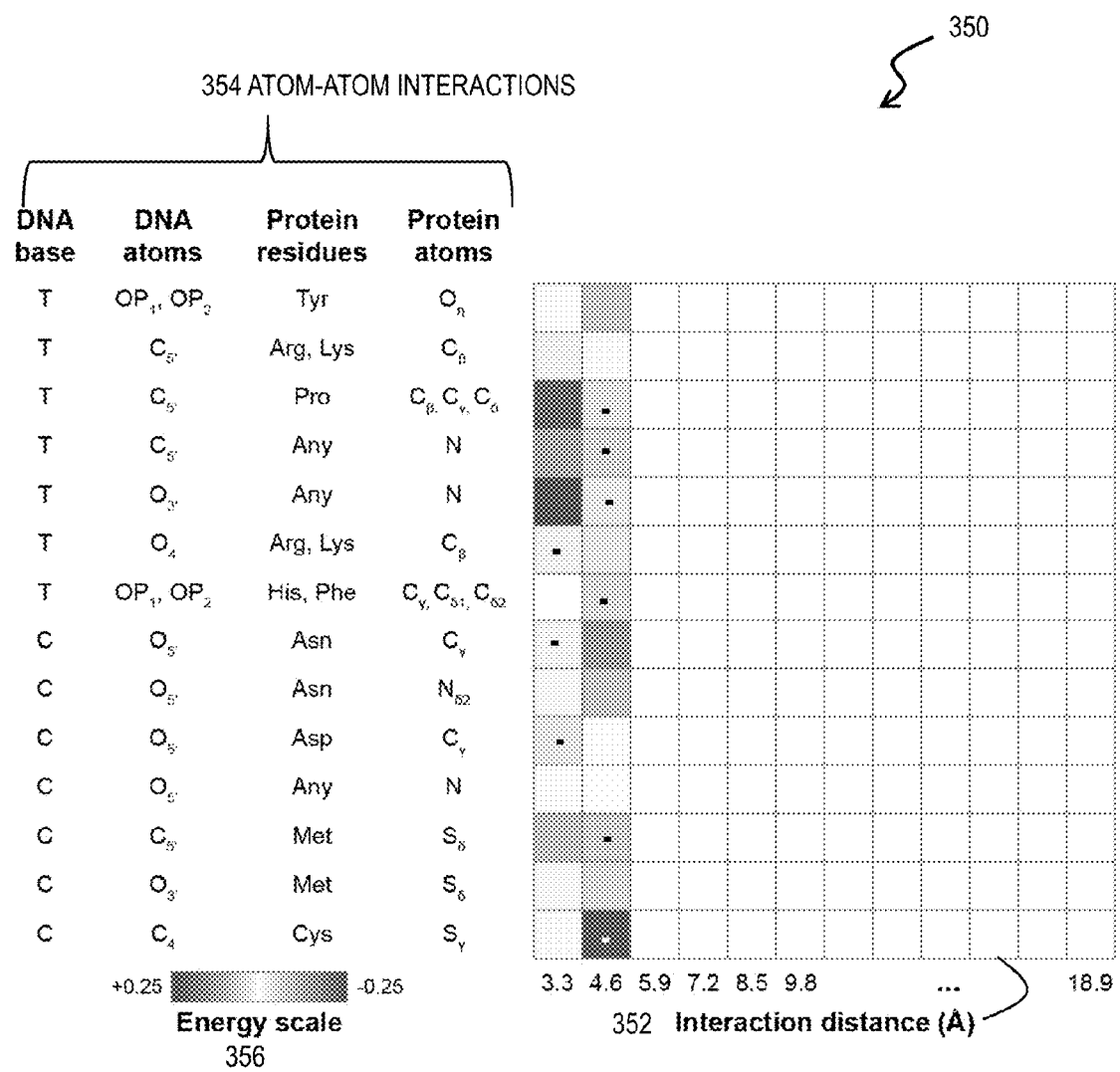
FIG. 3B is diagram that illustrates example values of a microscale interaction metric determined from values of a mesoscale interaction metric, according to one embodiment.

FIG. 3B is diagram 350 that illustrates example microscale interaction metric values determined from observations of mesoscale interaction metric values, according to one embodiment. The diagram 350 depicts the microscale metric (potential) values for various microscale interaction types represented by various distances of various particular atom pairs. The horizontal axis 352 in distance in Angstroms (Å). For this case, the distance bins had a width of 1.3 Å for all distances, except for the first bin which has a width of 3.3 Å. The vertical axis 354 is microscale interaction type (particular atom pairs). The atom pairs are indicated by the atom symbol (O for oxygen; P for phosphorous, C for carbon, N for nitrogen, S for sulfur) on a particular base of the DNA molecule (e.g., 110) followed by the atom symbol on a particular protein residue on the protein molecule (e.g., 120). The protein residues abbreviations are Tyr for tyrosine, Arg for arginine, Pro for proline, Any for any residue, Lys for lysine, His for histidine, Phe for phenylalanine, Asn for asparagine, Asp for aspartic acid, Met for methionine and Cys for cysteine. The grayscale 356 indicates the energy amplitude. The energy scale 356 is strictly relative. It can be used to compare the energy of one interaction to another, but it does not describe the absolute energy level of an interaction. This is sufficient for this embodiment, as only the relative energy levels are needed to infer the position weight matrix (PWM) that describes the binding affinity of proteins. In other embodiments, if the absolute energy levels are needed, they can be inferred by supplying the temperature at which the mesoscale interactions take place.

Energy values for atom-atom interactions at different distance ranges are indicated by the grayscale in each box, with negative energies indicated by a negative sign. Boxes with no grayscale (called blank boxes) are negligible in terms of contributing to the mesoscale protein-DNA binding energy.

FIG. 3B depicts the microscale interaction energies for the most energetic pairwise interactions found between protein and DNA atoms. For each interaction, the list of participant DNA and proteins atom are shown, along with the interaction energy at each distance bin. When more than one atom is listed for an interaction, it implies that the energy profile applies to any of the listed atoms. (The numerical subscripts identify particular atomic positions within the molecule in a standard nomenclature.) The interaction energies of each atom type are dependent upon its particular local context, including the presence of other atoms, which can yield non-intuitive results. The data shown in the figure corresponds to the current best microscale energy profile results. The fraction of interaction types with non-negligible energy for this particular energy profile was 3.29%. The large number of blank boxes indicates the solution space is sparse, consistent with compressive sensing.

Returning to FIG. 2A, in step 240 the solution results for the metric values of the set of microscale interaction types are validated against accepted values for the mesoscale metric that involve those interaction types. Evaluation and validation procedures are described in detail in a subsequent section, and confirm that the procedure works for protein-DNA binding. In some embodiments, in which the procedure is well accepted, step 240 is omitted.

In step 250, the values of the microscale metric for the multiple microscale interaction types are used. For example, a value for the mesoscale metric (e.g., binding energy or rate of occurrence) for a different mesoscale interaction (e.g., different protein-DNA binding) than the mesoscale interaction types used to derive the values of the microscale metric is predicted based on the derived values of the metric for the microscale interaction types. The correct predictions of such mesoscale metric values are demonstrated in subsequent sections.

Although steps are depicted in FIG. 2A as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

2. Detailed Methods

I is used herein to indicate the set of all possible microscale interaction types. A microscale interaction type may be as simple as two atoms existing within a predefined distance of one another, and as complex as a system of multiple molecules in conjunction with a solvent. Note that an interaction may depend on the distance of the interacting elements, in which case the same elements interacting at different distances would correspond to different interaction types in our formulation. Distance may be defined in terms of discrete distance ranges, or bins. For each microscale interaction type $i \in I$, we denote the value of its metric, such as its potential, by $e_i$.

K is used herein to indicate the set of mesoscale interaction types. As used herein, a mesoscale interaction type $k \in K$ is an observable-scale interaction where many microscale interactions combine to create the mesoscale interaction. For example, a protein to DNA binding is a mesoscale interaction comprised of all the energetic interactions occurring between protein atoms (or groups of atoms) and DNA atoms (or groups of atom). Formally, we associate with every mesoscale interaction $k \in K$, a vector $C_k \in \mathbb{Z}^{*|I|}$ where $\mathbb{Z}^{*|I|}$ is the set of positive integer vectors of dimension I. The vector $C_k$ contains for each $i \in I$ a count $C_{k,i}$ of the number of times that microscale interaction i is involved in mesoscale interaction k. For a microscale interaction type uninvolved in $k \in K$, its corresponding count is 0. Thus $C_{k,i}$ represents the weight of the ith microscale interaction in the kth mesoscale interaction. For each mesoscale interaction k we denote its metric, such as its energy or its relative frequency of occurrence, by $E_k$. By definition of mesoscale and microscale, they are related for at least some metrics, such as energy, as given in Equation 1.

$$E_k = \Sigma e_i C_{k,i} \text{ for all } i, i \in I \tag{1}$$

Using this notation, observations of the values of the metric $E_k$ for K mesoscale interaction types are used to determine the values of the metric $e_i$, any number of which serve as parameters for new models that predict values of the metric for other mesoscale interaction types, $E_j$, $j \notin K$, when $C_{j,i}$ is known or can be approximated.

Values for $e_i$ are inferred from measurements of $E_k$ using any method known in the art. In some embodiments, linear regression is used to infer the values of the microscale metric. In linear regression, an output variable is considered to be the sum of products of an input variable and unknown constant coefficients. In the context of the proposed method, the mesoscale interaction metric, $E_k$, serves as the response variable, and the count vector $C_{k,i}$ serves as the input variable, and the values of the microscale metric $e_i$ for $i \in I$ are the inferred coefficients. Within the compressed sensing framework, the values of the mesoscale interaction metric $E_k$ for all K provide the set of compressive measurements, the count vectors for all K provide the sensor matrix (set of sensors) that is the known function, and the set of values of the micro scale metric $e_i$ for all $i \notin I$ is the signal to be inferred.

If the values of the metric of mesoscale interactions cannot be observed directly, but their relationship to observables are known, such as relation of mesoscale binding energy to relative probabilities, then a constrained version of multinomial logistic regression can be shown to infer the values of the metric of the microscale interactions. An important feature of this embodiment is the use of a specific type of statistical mechanical ensemble, the canonical ensemble (see for example, McQuarrie D A, *Statistical mechanics*, University Science Books, Sausalito, Calif. pp xii, 641p, 2000).

An ensemble is a collection of physical states, for example the different structural conformations of a protein. In canonical ensembles, the temperature, volume, and number of particles are assumed identical across the states, but the energy may vary between states. In an illustrated embodiment, different mesoscale interactions correspond to different states of a canonical ensemble. For the protein-DNA binding problem, this corresponds to the protein binding to alternate DNA sequences with different binding energies. The probabilities of finding a system in each of the different states of a canonical ensemble follow the Boltzmann distribution. This property is exploited to reformulate $e_i$ determination as an instance of multinomial logistic regression. In this formulation, the relative probabilities of mesoscale interactions are used as experimental data. By relative probabilities is meant that the probability of a mesoscale interaction only has to be normalized with respect to two or more mesoscale interactions within the same canonical ensemble. Multiple distinct canonical ensembles can be used, and so not all mesoscale interactions need to come from the same canonical ensemble.

The general formulation is first derived, and then its formal equivalence is shown to multinomial logistic regression under appropriate constraint.

In this embodiment, K is the set of mesoscale interactions for which observations (described below) are available. K is partitioned into $\{K_1, K_2 \ldots K_L\}$ blocks such that mesoscale interactions within a block $K_l$ come from the same canonical ensemble, and there are L distinct canonical ensembles. In other words, for a fixed $1 \leq L$, for all $k \in K_l$, the temperature, volume, and number of particles are assumed fixed. Note that k is here used to refer to a mesoscale interaction within a given canonical ensemble.

For each canonical ensemble $K_l$, measurements are taken corresponding to the relative probabilities $p_k$ of every measured mesoscale interaction for all $k \in K_l$, in the ensemble. In other words, for all $1 \leq L$, the measured probabilities obey Equation 2.

$$1 = \Sigma p_k \text{ for all } k \in K_l \tag{2}$$

Since by definition all mesoscale interactions $k \in K_l$ come from the same canonical ensemble, then the measured probability $p_k$ of a given mesoscale interaction k is related to an energy metric of the mesoscale interactions as described by the Boltzmann distribution given by Equation 3a and 3b.

$$p_k = Z_l^{-1} \exp(-\alpha_l E_k) \tag{3a}$$

$$Z_l = \Sigma \exp(-\alpha_l E_k) \text{ over all } k \in K_l \tag{3b}$$

Where exp( ) indicates the exponential function of the base of the natural logarithm raised to the power of the argument inside the parentheses, $E_k$ here is the energy metric of the mesoscale interaction, $Z_l$ is the partition function of the canonical ensemble $K_l$, and $\alpha_l$ is the inverse temperature parameter for the ensemble (not following the standard convention of using $\beta$ for the inverse temperature).

Given a set of mesoscale interactions K for which the constituent microscale interactions I are known, and a partitioning of the mesoscale interactions such that the probabilities $p_k$ are known for all $1 \leq L$, the energies $e_i$ of the microscale interactions I can be inferred. The derivation is not shown here, but involves the steps of substituting into Equation 3a for $Z_l$ using Equation 3b, substituting for $E_k$ using Equation 1, and re-arranging the terms to give a system of equations given by Equation 4.

$$p_k = \{\Sigma j \in K_l \exp[\alpha_l \Sigma i \in I\ e_i(C_{k,i} - C_{j,i})]\}^{-1} \tag{4}$$

This system of equations can be solved for $e_i$ for $i \in I$. In some embodiments, the inverse temperature parameters $\alpha_l$ are treated as free parameters; and, in other embodiments the inverse temperature parameters $\alpha_l$ are experimentally known temperatures of the mesoscale interactions.

In some embodiments, Equation 4 is recast as a constrained version of multinomial regression. For this formulation, the inverse temperature parameters $\alpha_l$ are advantageously known a priori. For biological applications it is assumed that interactions occur under "standard biological conditions" (e.g., see Berg J M, Tymoczko J L, & Stryer L *Biochemistry*, W.H. Freeman, New York, 6th Ed., 2007). Furthermore, for simplicity of derivation without loss of generality, it is assumed that the set K is partitioned into blocks of equal size of cardinality M and indexed such that the first M mesoscale interactions are in $K_1$, the second M mesoscale interactions are in $K_2$, and so forth, yielding $\{k=1,M\}=K_1$, $\{k=M+1, 2M\}=K_2, \ldots, \{k=(L-1)M+1,LM\}=K_2$. No loss of generality results from such a partitioning since zero-probability mesoscale interactions (e.g. all atoms are in the same position) can be used to pad canonical ensembles to be of equal size.

Using this partitioning, each canonical ensemble $K_l$ can then be treated as a single data point in an M-class multinomial regression problem, with the regression input vectors $\{X_l \in \mathbb{R}^{I(M-1)}\}_{1 \leq l \leq L}$ (where $\mathbb{R}^{I(M-1)}$ is the set of real-valued vectors of dimensionality $1(M-1)$) having the form given by Equation 5a.

$$X_l = \{\alpha_i(C_{M,i} - C_{M(l-1)+m,i})\} \text{ for } i \in I, 1 \leq m \leq M-1 \quad (5a)$$

Together, the input vectors $X_l$ define the design matrix X as given by Equation 5b.

$$\{X_l\}_{1 \leq l \leq L} = X \in \mathbb{R}^{L \times I(M-1)}. \quad (5b)$$

(where $\mathbb{R}^{L \times I(M-1)}$ is the set of real-valued vectors of dimensionality $L*1(M-1)$). The output vectors $\{Y_l \in \mathbb{R}^{M-1}\}_{1 \leq l \leq L}$ have the form given by Equation 5c.

$$Y_l = \{p_{M(l-1)+m}\}_{1 \leq m \leq M-1} \quad (5c)$$

Together, the output vectors $Y_l$ define the output matrix Y as given by Equation 5d.

$$\{Y_l\}_{1 \leq l \leq L} = Y \in \mathbb{R}^{L \times (M-1)} \quad (5d)$$

Using this formulation, the multinomial logistic regression problem is expressed by Equation 6.

$$Y_{l,m} = \frac{e^{X_l \beta_m}}{1 + \sum_{n=1}^{M-1} X_l \beta_n} = \frac{e^{\sum_{p=1}^{I(M-1)} \beta_{m,p} X_{l,p}}}{1 + \sum_{n=1}^{M-1} e^{\sum_{p=1}^{I(M-1)} \beta_{n,p} X_{l,p}}} \quad (6)$$

where $\beta_{m,p}$ is the pth coefficient of the mth class in the regression coefficient matrix, and $Y_{l,m}$ is the output of the mth class for the lth data point. The $M^{th}$ class is treated as the comparison category in the regression.

Two constraints are introduced here, which, when enforced, make the statistical mechanical model of Equation 4 and multinomial logistic regression of Equation 6 equivalent. The two constraints are given by Equations 7a and 7b.

$$\forall m \in [1, M-1], p \notin [I(m-1)+1, Im]: \beta_{m,p} = 0 \quad (7a)$$

$$\forall m,n \in [1, M-1], i \in [1, I]: \beta_{m,I(m-1)+i} = \beta_{n,I(n-1)+i} \quad (7b)$$

By letting k be the $m^{th}$ mesoscale interaction of the $l^{th}$ partition of K, and noting the identity of Equation 7c $$\forall l: K_l = [M(l-1)+1, Ml], \quad (7c),$$

it can be shown that Equation 6 leads to Equation 4 where $Y_{l,m} = p_k$ and the inferred coefficient $\beta_i = e_i$ for all $i \in I$. This demonstrates equivalence of the statistical mechanical model to multinomial logistic regression, when the constraints are applied. This shows that the multinomial logistic regression of Equation 6 is used when the mesoscale metric is a probability. Additional constraints can be placed to exploit prior knowledge about the microscale interactions. For example, if the microscale interactions are known to be sparse in a certain basis, then they can be transformed to that basis. Furthermore, if the matrix of microscale interaction is known to be low-rank, then that constraint can be placed as well. In general, constraints encoding prior knowledge about the problem can be added to the formulation provided above.

This is an important result in the proposed method formulation. Once it is demonstrated that the de novo atom/atom complex energy determination problem can be cast as a regression problem, the methods of compressed sensing can be considered to be applied to solve the regression problem.

Compressed sensing is a theoretical and applied framework that enables the recovery of a signal with high accuracy from relatively few measurements. In the context of the example regression formulation, the signal is the set of values of the microscale interaction metric $\{e_i\}_{i \in I}$, (whether representing energy or some other aspect of the microscale interactions), the sensors are the K mesoscale interaction types $\{E_k\}_{k \in K}$, such as protein-DNA or protein-protein binding events, and the measurements are the energies or relative probabilities of the mesoscale interaction types. Compressed sensing enables the use of relatively few measurements to infer the energies of the microscale interaction types underlying the mesoscale interaction types.

The application of compressed sensing to regression is achieved by imposing an $l_1$ regularization penalty on the regression problem (e.g., see Tibshirani R "Regression shrinkage and selection via the Lasso," *J Roy Stat Soc B Met* v58 no. 1, pp 267-288, 1996.). Several compressed sensing approaches have been developed to accomplish this task. In an illustrated embodiment, the lasso penalty for linear regression is utilized with its generalization for logistic regression (e.g., see Friedman J, Hastie T, & Tibshirani R "Regularization Paths for Generalized Linear Models via Coordinate Descent," *J Stat Softw* v33 no. 1, pp 1-22, 2010). In other embodiments, other approaches are utilized, such as the Dantzig selector (e.g., see Candes E & Tao T "The Dantzig selector: Statistical estimation when p is much larger than n," *Ann Stat* v35 no. 6, pp 2313-2351, 2007) for linear regression and suitable generalizations for logistic regression (e.g., see James G M & Radchenko P "A generalized Dantzig selector with shrinkage tuning," *Biometrika* v96 no. 2, pp 323-337, 2009). Other generalizations that capture related notions of sparsity, for example, the nuclear norm penalty (e.g., see E. J. Candès and B. Recht, "Exact matrix completion via convex optimization," *Found. of Comput. Math.*, v9, pp 717-772, 2008) for low-rank matrices is used in some embodiments. Any penalty known in the art may be used.

For example, using the lasso penalty embodiment, one would solve the optimization problem given by Equation 8.

$$\min_e \|Ce - E\|_2^2 + \lambda \|e\|_1 \quad (8)$$

Accurate inference of potentials is ultimately dependent on two important characteristics of the particular application. These two characteristics are the sparsity of the microscale interaction metric to be inferred, and the coherence of the mesoscale interaction measurements used for inference. The compressed sensing literature contains many theoretical guarantees about the expected number of measurements required, denoted by m, given a signal of length n with s non-zero entries and a sensor matrix X with coherence μ (the design matrix in regression). The majority of these results concern sensor matrices with some degree of randomness (e.g., see Candès E & Plan Y "A Probabilistic and RIPless Theory of Compressed Sensing," *IEEE Transactions on Information Theory*, v57, no. 11, pp 7235-7254, 2010). In the illustrated embodiment, the sensor matrix is fixed and defined by the set of K mesoscale interaction types in the data set. Theoretical guarantees for fixed matrices are also discussed (e.g., see Candes E J & Romberg J "Quantitative robust uncertainty principles and optimally sparse decompositions," *Found Comput Math* v6, no. 2, pp 227-254, 2006; and Tropp J A, "On the conditioning of random subdictionaries," *Appl Comput Harmon A* v25 no. 1, pp 1-24, 2008).

In general, most results relate m to an increasing function of n, s, and μ. In the context of the illustrated embodiment, n is the total number of possible microscale interactions, s is the number of microscale interaction types $I_0 \subset I$ whose values are non-negligible, i.e. for all $i \subset I_0$, $e_i \gg 0$, and μ is the coherence of the sensor matrix X. Thus, if only a small number of the microscale interaction types are non-negligible (i.e., s is small), then only a small number of measurements are needed for accurate inference of the metric value. The role that μ plays is slightly more subtle (the formal definition of μ can be found in Candes E J & Wakin M B "An introduction to compressive sampling," *IEEE Signal Proc Mag* v25, no. 2, pp 21-30, 2008.). Intuitively, coherence relates to the diversity of microscale interactions that constitute each mesoscale interaction. The greater the variety of microscale interactions participating in each experimentally characterized mesoscale interaction, the smaller the coherence. Thus, to minimize the number of experimental measurements needed, one needs to minimize the coherence of the sensor matrix. This implies that the mesoscale interaction types must incorporate as wide a range of microscale interaction types as possible. However, the degree to which the coherence of mesoscale interactions can be controlled is dependent on the application. For biological systems, the choice of biomolecules comprising the set of mesoscale interactions directly impacts the coherence of the sensor matrix.

In some embodiments, the regression equations of Equation 6 are solved using methods of compressed sensing. All regressions are regularized using the lasso penalty. Additionally, all mesoscale interactions are assumed to occur under "standard biological conditions" so that there is a common temperature across all ensembles. Because the temperature is fixed, it can be factored out of the inferred microscale metric values, and so it is set equal to 1 to simplify the calculations.

The microscale interactions include two spatial metaparameters: binning width and cutoff distance. Binning width corresponds to the resolution at which contact distances are made discrete. Cutoff distance is the distance beyond which interactions are ignored. A third parameter, known as the regularization parameter λ (1), adjusts the expected degree of sparsity of the microscale interaction types with non-negligible values. Values for these parameters are determined by fitting procedure using a training dataset where the values of the microscale metric, the mesoscale metric and the function (e.g., weights of the weighted sums) are known.

An $l_1$-regularized multinomial logistic regression is performed using commercially available software, such as the R-based glmnet package (e.g., see Friedman J, Hastie T, & Tibshirani R "Regularization Paths for Generalized Linear Models via Coordinate Descent," *J Stat Softw*, v33, no. 1, pp 1-22, 2010) available online at subfolder i01 of folder v33 at World Wide Web (WWW) domain jstatsoft in domain category org. Solutions for the constrained regression problem Equation 6, Equation 7a and Equation 7b are feasible for the unconstrained regression problem, Equation 6 alone. Consequently, the constraints are not enforced in the illustrated embodiments to provide the technical advantage of greater computationally efficiency. It is anticipated that enforcing the constraints is unlikely to greatly improve accuracy of the results.

3. Example Embodiments

Example embodiments described here in detail are directed to protein-DNA interactions. This embodiment casts microscale potential determination as a compressed sensing problem.

For the protein-DNA example embodiment, the coherence of the sensor matrix is dependent on the set of protein-DNA complexes used as mesoscale interactions. For a given set of protein-DNA complexes whose atomic structures have been determined, the coherence μ can be computed from the counts of atomic interactions present in the structures. This provides a principled approach for choosing new protein-DNA complexes for crystallization, based on their predicted atomic structures and the resulting value for μ. By carefully selecting protein-DNA complexes that yield the smallest predicted coherence of the sensor matrix, the accuracy of the inferred protein-DNA potential can be increased with a small number of targeted crystallization experiments.

Several different embodiments for microscale potential determination are presented. The details common to all inferred protein-DNA embodiments are described first, and then the baseline microscale potential embodiment and embodiments for modified microscale potentials that relax physical constraints are described.

In all protein-DNA potentials in this section, the microscale interactions are defined as pairwise contacts between DNA and protein atoms at specified distance ranges. Intra-DNA interactions, known as indirect readout, are ignored, as are intra-protein interactions. We use the atom classification scheme of the Quasichemical potential (e.g., see Donald J E, Chen W W, & Shakhnovich E I "Energetics of protein-DNA interactions," *Nucleic Acids Res* v35 no. 4, pp 1039-1047, 2007), which takes into consideration the chemical identity of the atom as well as its local moiety. In this scheme there are 37 DNA atom types and 27 protein atom types. Contact distances are categorized into bins of fixed width (described below). Thus, a model with D distance bins contains a total of 37×27×D interaction types. The potential inference problem is to determine the value of the energy metric of each of these microscale interaction types using experimental measurements of mesoscale interactions, specifically protein-DNA binding events. As described below, these binding events are based on protein-DNA crystal structures and their associated binding energies.

For this inference problem, the multinomial logistic regression approach of Equation 6 is used. The canonical ensembles are created by fixing the protein and varying the DNA sequence in computer simulations (called in silico) by substitution of the alternative nucleic acids at each site in the interaction region as described in the next paragraph. The conventional assumption is made that the DNA basepair positions in the interaction region are independent; and, each set of protein-DNA basepair complexes derived from separate protein-DNA crystal structures is treated as a separate canonical ensemble. Thus each ensemble is comprised of four mesoscale interactions, corresponding to one protein binding to each of the four possible nucleotide basepairs. Previous studies have provided justification for treating such ensembles as canonical ensembles.

The observations are obtained from experimental data of crystallized protein:DNA structures in conjunction with their experimentally determined DNA binding motifs. A single protein-DNA binding event corresponds to a protein-DNA basepair complex. For the regression input vectors, the function, e.g., weights of the weighted sums given by the counts of the interaction types as defined above, is assumed known or approximated for each protein-DNA binding event. In the illustrated embodiments, these counts are determined from the atomic coordinates of protein and DNA atoms in the x-ray crystal structures of protein:DNA complexes. For each protein:DNA crystal complex, in silico structural mutants are generated so that every basepair in each DNA position is in silico mutated to every possible alternative nucleotide and the associated mesoscale interaction energy is computed. (For example, if there is an "A" at a particular position, the three alternative structures with "T", "G", and "C" at that position are constructed.) Thus, for each protein:DNA complex with a DNA sequence of length N, a total of 4N structures and associated mesoscale metric values are obtained which are grouped into N canonical ensembles as previously described.

For the regression output vectors, values of the mesoscale metric for each mesoscale interaction type, the relative probabilities of the mesoscale interaction events within each canonical ensemble are obtained from observations. These relative probabilities correspond to the probabilities with which a protein binds to the four DNA nucleotides at a given position. When inferring a protein-DNA potential to predict consensus sequences from the crystal structures, the probability of binding to the nucleotide observed in the structure is set to 1, and the probability of binding to any other nucleotide is set to 0. A consensus sequence is a sequence of DNA nucleotides (bases) where a particular protein is most likely to bind to a DNA helix, as found by experiment. When inferring a protein-DNA potential for predicting position weight matrices (PWMs), the probabilities are derived from experimentally determined PWMs that are manually curated for each protein:DNA complex in the data set. A PWM is a set of probability distributions, one for each basepair position in the DNA binding site, over the four possible DNA nucleotides. The probability assigned to each protein-DNA binding event is the value of that event given in the experimental PWM.

A set of HTH:DNA complex structures from the Protein Data Bank (e.g., see Berman H M, et al., "The Protein Data Bank," *Nucleic Acids Res* v28, no. 1, pp 235-242, 2000) were obtained by searching for x-ray crystal structures that contain an HTH domain and DNA molecules. Complexes were considered to be redundant if they shared the same sequence of amino acids within a 10 residue window of the recognition α helix, and only one representative for such complexes was retained. This criterion was chosen due to the dominant role that recognition α helices play in effecting the sequence specificity of HTH proteins, and the fact that HTHs with otherwise highly similar sequences may still exhibit differential DNA binding properties. In addition, complexes with pathologies such as a large number of missing heavy atoms in the published structure were removed. The resulting data set is comprised of 63 non-redundant HTH:DNA complexes. For each of the HTH:DNA complexes in this data set, a PWM was derived based on experimental data curated from multiple sources.

3.1 Baseline Microscale Potential Embodiment

The baseline protein-DNA potential uses differences of counts of microscale interactions as the regression input vectors, as given above in Equation 5a. In the illustrated embodiment, one state within each canonical ensemble is used as a comparison category, where the states correspond to the four nucleotides. Guanine was arbitrarily chosen for this purpose.

In the crystal structure data set, it was found that only 9% of microscale interaction energies were non-negligible. This satisfies the condition for a sparse signal. Regarding the incoherent measurements, the energies of mesoscale interactions are incoherent measurements, because (i) they are the summed energies of the microscale interactions and thus integrate the intensity of multiple vector elements, and (ii) the set of microscale interactions present in each mesoscale interaction is highly variable, as shown above in FIG. 3A.

Because the sensor vector elements for each measurement must be known or estimated, the microscale interactions comprising each mesoscale interaction must be known or estimated. Protein-DNA crystal structures provide a data set of mesoscale interactions whose constituent microscale interactions are identified from the positions of the protein and nucleotide atoms in the contact regions of the structure. The set of 63 non-redundant structures, combined with their measured binding affinities, were used as the data set for the de novo microscale potential determination described. The non-redundancy of these structures ensures that each mesoscale interaction samples a different set of microscale interactions, since the intrinsic variability of the structures due to their varying spatial conformations and different amino acid compositions results in high variability in the microscale interactions that constitute each mesoscale interaction. (The degree of incoherence is quantified in FIG. 3A). Now, because this method recasts potential determination as a compressed sensing problem, only a small number of incoherent measurements, i.e. experimentally characterized protein-nucleotide binding events, are needed. This circumvents the experimental combinatorial explosion problem cited earlier.

In the protein-DNA embodiment, a collection of protein-nucleotide complexes in which the protein is fixed and individual nucleotides are varied forms a canonical ensemble, and the protein's relative binding probabilities to different nucleotides are the experimental data (observations). These probabilities are obtained from experimentally-determined position weight matrices (PWMs) of protein binding sites or from consensus binding sequences by assuming that consensus nucleotides bind with 100% probability.

The probability-based formulation of Equation 6 was used to determine the protein-DNA potential of helix-turn-helix (HTHs) proteins and predict their consensus binding sequences and PWM motifs. The effort focused on HTH proteins because they are the most widely distributed family of DNA-binding proteins, occurring in all biological kingdoms, with a large number of structures in the Protein Data Bank. HTH proteins include virtually all bacterial transcription factors and about 25 percent of human transcription factors. For the prediction of consensus binding sequences, the microscale potential is inferred using probabilities derived from the consensus sequences of protein-DNA structures in a data set reserved for training the algorithm. A separate set of protein-DNA structures is used to test predictions made with the inferred potential.

For each protein-DNA structure in the test set, every DNA sequence position is mutated in silico to every possible pair of nucleotides, and the relative binding affinities of the mutated structures are computed. In silico mutagenesis was carried out using the 3DNA software package available online at domain x3dna of domain category org, which maintains the backbone atoms of the DNA molecule, but replaces the basepair atoms in a way that is consistent with the backbone orientation in the crystal. Independence of DNA positions was assumed; and this process was repeated for every position.

The most probable nucleotides at all positions are predicted with 12.9% error, compared to 42.1% error by the leading alternative method. Alternative methods are compared in Table 2, below. For the more complex problem of predicting quantitative PWMs, the potential was determined using probabilities derived from published experimentally-determined PWMs of the 63 protein-DNA structures in the data set. Compared to leading physical and statistical potentials, the de novo microscale potential of the illustrated embodiment produces the best PWM score using the symmetric Kullback-Leibler divergence (SKLD) metric. Note that the second and third best performing potentials require consensus binding sequences as input. Providing that input significantly simplifies the problem, whereas the illustrated embodiment infers the consensus binding sequences.

3.2 Transformed Inputs

Also considered were two generalizations that relax physical constraints, yielding pseudo potentials which perform better in practice. This embodiment uses transformed input vectors.

The "transformed inputs" protein-DNA potential uses ratio of counts of microscale interactions as the regression input vectors. Specifically, the regression input vectors $\{X_l \in \mathbb{R}^{IM}\}_{1 \leq l \leq L}$ are given by Equation 9.

$$X_l = \left\{ \alpha_i \left( \frac{C_{M(l-1)+m,i}}{\sum_{n=1}^{M} C_{M(l-1)+n,i}} \right) \right\}_{i \in I, 1 \leq m \leq M} \quad (9)$$

In this protein-DNA potential all elements of the regression input vectors are also standardized such that their mean is zero and variance is one. Input vectors with this property typically exhibit better statistical properties.

3.3 Region Specific Energy Profiles

Distinct microscale potentials were determined for interactions occurring in different regions of the HTH-DNA binding interface, motivated by the observation that binding affinity is strongest in the core region of the binding interface and gets progressively weaker away from the core region.

In the "region-specific" protein-DNA potential, the energies of microscale interactions are allowed to vary as a function of position along the protein-DNA binding interface. The motivation behind this generalization is addressed first, followed by a description of how region-specificity is incorporated into the protein-DNA energy regression.

A microscale interaction energy metric typically defines an interaction energy metric independently of the position of the interaction along the molecule. This is a desirable property when the position has no bearing on the energetics. However, if the position of the interaction is indicative of a consistent physico-chemical environment, properties of this environment can be exploited when modeling the energies of interactions. This is usually exploited on a small-scale, for example by treating two carbon atoms as distinct atom types depending on their chemical moiety, as in the C1' and C2' atoms of DNA. In that case, the carbon atom's local chemical moiety is the consistent physico-chemical environment, and it is used in modeling the system to influence the interaction energies of the atoms, by treating carbon atoms with distinct chemical moieties as distinct atom types.

For protein-DNA potentials, it was investigated whether this notion could be generalized to a larger spatial context, by deriving a Microscale interaction energy metric where the microscale interaction energies are allowed to vary as a function of position along the protein:DNA binding interface. A key requirement for such a metric to work is that any given position along the binding interface must exhibit a consistent physico-chemical environment across structures, for example to have essentially the same steric constraints. For the protein-DNA potential, it was hypothesized that this is the case when a set of proteins employ the same binding modality for docking into DNA, as is often true for members of the same protein family. It is anticipated that a region-specific model may be suitable for the Helix-turn-helix proteins (HTH) family, because (i) the sequence-specificity of HTHs is largely mediated by interactions between the DNA and the recognition $\alpha$ helix of HTHs, and (ii) the relative orientation of the two core $\alpha$ helices that make up the HTH domain is conserved across HTH families, despite the broad structural diversity of HTH domains.

All 63 HTH:DNA complexes in the data set were aligned by structure so that the DNA molecules are superimposed and the variation in the orientation and position of the recognition helices is minimized. Formally, if $RMSD_{DNA}$ is the root mean square deviation (RMSD) between the backbone carbon atoms of two aligned DNA molecules, and $RMSD_{HTH}$ is the RMSD between the $C^\alpha$ atoms of two aligned HTH recognition helices, then alignment is achieved by minimizing $RMSD_{HTH}$ subject to $RMSD_{DNA} < \delta$. For the illustrated embodiment, $\delta$ was set to 2 angstrom (Å).

Figure 4:
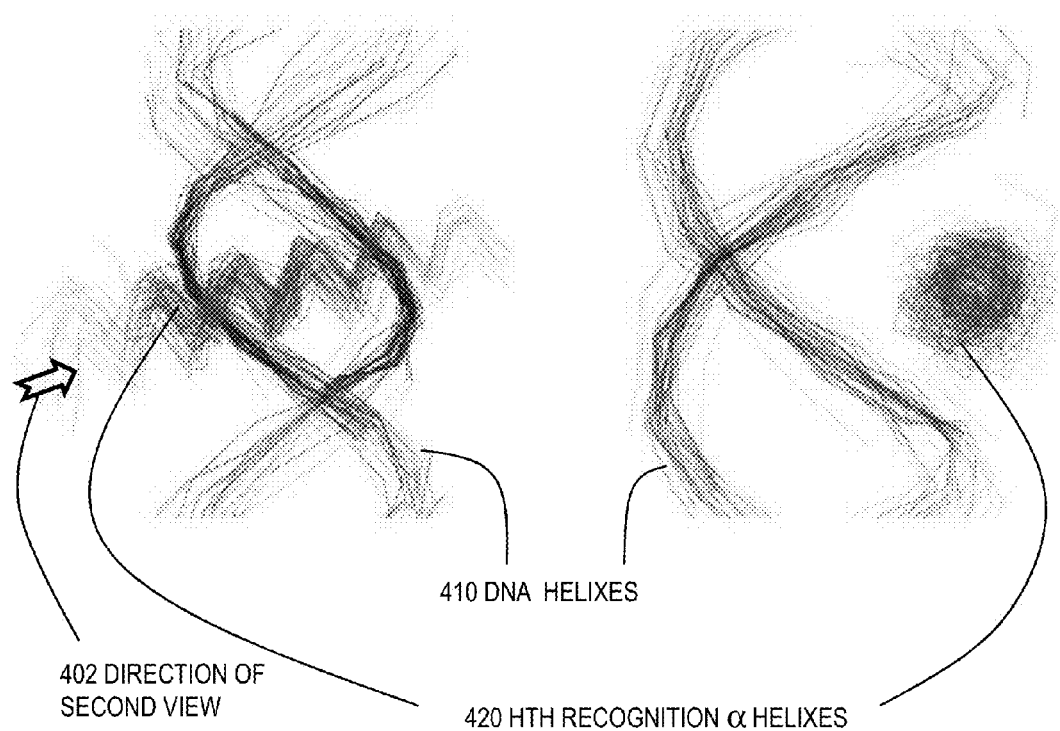
FIG. 4 is a block diagram that traces the HTH recognition α helix S320 and DNA helix S310 for each of 63 different HTH:DNA complexes after alignment.

Any HTH:DNA complex in the data set can be used as a baseline for a multiple alignment, so the complex that minimizes the average $RMSD_{HTH}$ to all other complexes was selected. The resulting multiple alignment, shown in FIG. 4, produces a unified coordinate system along the HTH:DNA binding interface such that the physico-chemical environment at a given spatial position is comparable across all structures. FIG. 4 is a block diagram that traces the HTH recognition $\alpha$ helix 420 and DNA helix 410 for each of 63 different HTH:DNA complexes after alignment, according to an embodiment. The left view is from a first direction, and the right view is in a perpendicular direction indicated by arrow 402.

To exploit this alignment in the determination of the protein-DNA potential, the resolution of the coordinate system is reduced to the level of individual DNA basepairs. In other words, the number of distinct positions in the coordinate system is made equal to the number of distinct DNA basepair positions in the HTH-DNA binding interface. In this way, a DNA base in one HTH:DNA complex is comparable with exactly one other DNA base in every other complex. In total there are 13 distinct DNA basepair positions, encompassing the largest observed HTH:DNA binding interfaces in the data set.

To incorporate region-specificity into the inferred protein-DNA microscale metric values, the elements of every regression input vector are duplicated 13 times. Formally, the regression input vectors have the form of Equation 10.

$$X_l^{(n)} = \{\alpha_i(C_{Ml,i} - C_{M(l-1)+m,i})\}_{i \in I, 1 \leq m \leq M-1} \cup \{1\{r=n\} \\ \alpha_i(C_{Ml,i} - C_{M(l-1)+m,i})\}_{i \in I, 1 \leq m \leq M-1, 1 \leq r \leq 13} \quad (10)$$

In this formulation, the original set of elements in the input vectors are left unchanged, and the nth duplicate set in an ensemble representing the nth DNA basepair is also left unchanged. All other vector elements are set to 0. $X_l^{(n)}$ is a canonical ensemble that corresponds to a binding event at the nth DNA basepair position, and $1\{r=n\}$ is the indicator function testing whether r equals n. This encoding of the regression input vectors allows the inference algorithm to model the shared interaction energies common across all positions, as well as including position-specific adjustments among the microscale interaction types.

3.4 Predicting Values for Metric of Different Mesoscale Interaction Types

In this section the de novo values of the microscale metric (potential) for protein-DNA microscale interaction types derived in one of the above embodiments are used to predict the values of the mesoscale metric (binding energy) for a different mesoscale interaction type, and, as a consequence, predict a DNA binding site of a protein. This is accomplished by first using the inferred protein-DNA microscale energy values to compute the binding energies of the protein:DNA structures, and then using those computed energies to predict the DNA binding sites of proteins that produces the strongest binding. The structure-based approach to binding site prediction is first described; and then the testing methodology and quality indicators used are detailed.

Starting with a protein:DNA x-ray crystal structure, structure-based methods transform the structure into a set of microscale interactions (in the illustrated embodiment, a count-weighted sum of certain protein atom to DNA atom contacts). Once the set of microscale interactions are identified, the overall binding energy of a protein:DNA structure is computed by adding up the individual energetic contributions from all the microscale interactions observed in the structure. How the interaction energies are defined depends on the choice of potential used; in the illustrated embodiment, the de novo protein-DNA microscale potential values described above are used to compute the binding energies. Formally, if I is the set of all interactions observed in a structure, $e_i$ is the energetic contribution of interaction i, $C_i$ is the number of times interaction i is observed in the structure, then the binding energy of the structure, denoted by $\Delta G$ is given by Equation 1, where $\Delta G$ is the mesoscale metric $E_k$ and k indicates the current different mesoscale interaction type k.

The relative affinity of a protein to two different DNA sequences can be evaluated by computing the binding energy of the protein to those two sequences. This is done by fixing the protein in the protein:DNA complex and mutating the DNA sequence in silico. To make this problem computationally tractable, it is assumed here, as is often assumed, that the energetics for one DNA position in the binding interface can be computed separately from other positions. Doing so simplifies the computation by involving for a DNA sequence of length N only 4N energetic calculations, where each basepair in the DNA is mutated in silico to every possible nucleotide independently from other basepairs, and the binding energy of each of these in silico mutated protein:DNA structures is computed. Using the computed binding energies, the Boltzmann formula of Equations 3a and 3b can then be used to compute the probability of observing nucleotide m at position n, denoted by $p_m^{(n)}$. Equation 3a and 3b are used at position n, with k=m indicating the nucleotide base at position n, $K_j$ is the set of the four nucleotide bases {A, C, G, T} at position n, and $E_m = \Delta G_m$, is the binding energy of the structure when nucleotide m is at position n. For computation of relative energy when temperature is constant, $\alpha_j$ is set equal to 1. Performing this computation for every position n and every nucleotide m yields the predicted position weight matrix (PWM) for the DNA binding sites of the protein. When the consensus sequence is to be predicted, the most probable nucleotide at every position is chosen as the consensus nucleotide.

3.5 Validation Methods

In some embodiments, step 240 is included to validate the results (e.g., the values of the microscale metric for the set of microscale interaction types, or the most probable nucleotide at a position, or the most probable binding sites for a protein on a given DNA molecule).

To test the results from step 230 or 250, 9-fold cross validation (CV) was used. The 63 complexes were split into 9 groups of 7 complexes each. Each group yielded a testing configuration where 7 complexes comprise the test set, and the remaining 56 the training set. The model was trained on the training set and tested on the test set using all 9 testing configurations, and the average was taken over all test sets. Since some metaparameters vary the number of degrees of freedom in the model, fitting them strictly on the training set was not successful, as the algorithm would always maximize the number of degrees of freedom. Consequently the 3 metaparameters were fit by finding the value that minimizes average error over all test sets. Results are shown in FIG. 5A, FIG. 5B, FIG. 6A, FIG. 6B and Table 2. In the illustrated embodiment, the best fit produced values of the binning width as 1.3 Å, the cutoff distance as 5.9 Å, and λ as 0.00113821.

In some embodiments of step 240, an objective was to provide a consistent testing environment for all methods considered for comparison with the results of step 230 or step 250. When original comparison/validation code implementations were available, they were used; otherwise the method considered was implemented from equations, as for the Quasichemical potential. Recommended default settings were chosen when applicable, and all parameter settings fit using the original methods' data sets were left unchanged. For the Rosetta potential, the energetic terms were set to the following values: fa_atr=0.947733, fa_rep=0.577238, hb_sc=1.596235, gb_elec=0.203353, fa_sol=0.507356, dna_bs=0.1, and dna_bp=0.1. These values are based on the fitted parameters from Morozov A V, Havranek J J, Baker D, & Siggia E D, "Protein-DNA binding specificity predictions with structural models," *Nucleic Acids Res* v33, no. 18, pp 5781-5798, 2005. Depending on the original data sets used for training each algorithm, some methods may have an advantage over other methods if their training data set included structures that were also in the curated test sets. Nonetheless, given the heterogeneous set of methods tested and their reliance on different types of input data, the methodology used provided a consistent and objective comparison.

When testing the consensus sequence predictions of the Rosetta algorithm and the DNAPROT algorithm (latter from, Angarica V E, Perez A G, Vasconcelos A T, Collado-Vides J, & Contreras-Moreira B, "Prediction of TF target sites based on atomistic models of protein-DNA complexes," *Bmc Bioinformatics*, v9, no. 1, p436, 2008), their indirect readout components had to be disabled as they explicitly rely on the consensus sequence itself as input. For Rosetta, this was done by setting the dna_bs and dna_bp terms to zero weight, to eliminate the indirect readout component from the potential. For DNAPROT, this was done by running it with the setting "-p' -P -1 -e -c -D 0'", which disables DNAPROT's indirect readout component and its Cumulative Contacts component (from Morozov A V & Siggia E D "Connecting protein structure with predictions of regulatory sites," *P Natl Acad Sci USA* v104, no. 17, pp 7068-7073, 2007), both of which rely on the consensus sequence as input.

3.6 Comparisons with Other Methods

We tested these generalizations individually and in combination as shown in Table 2, below. Performance is assessed based on predictions of consensus sequences and PWMs averaged over the 63 structures in the data set. For consensus sequence prediction, error is measured by the percentage of incorrectly predicted bases. For PWM predictions, the average SKLD over all DNA positions is reported (lower is better). A random model in which all DNA basepairs are assumed to be equally likely is also shown for reference.

TABLE 2

Performance of de novo microscale potential and other leading atom-atom potentials.

| | | | Prediction Quality | |
|---|---|---|---|---|
| Potential | Type | Intra-DNA Interactions | Consensus Sequence Error | PWM Symmetric KL Divergence |
| Random Model | N/A | N/A | 75% | 3.335 |
| Methods Requiring Consensus Sequences | | | | |
| Rosetta (12) | Physical | Yes | N/A | 2.632 |
| Cumulative Contacts (13) | Statistical | No | N/A | 2.033 |
| DNAPROT (14) | Statistical | Yes | N/A | 1.991 |
| Methods Not Requiring Consensus Sequences | | | | |
| DNAPROT* (14) | Statistical | No | 60.2% | 3.279 |
| Rosetta* (12) | Physical | No | 50.8% | 2.719 |
| Quasichemical (6) | Statistical | No | 42.1% | 2.248 |
| De novo Methods (Do Not Require Consensus Sequences) | | | | |
| Baseline | De Novo | No | 12.9% | 1.960 |
| Transformed Inputs | De Novo | No | 10.2% | 1.861 |
| Region-Specific Potentials | De Novo | No | 13.7% | 1.792 |
| Both Generalizations | De Novo | No | 10.1% | 1.699 |

*Only the direct readout components of potentials are used in those tests since they do not require consensus sequences as input.

The consensus sequence predictions are slightly improved (10.1% vs. 12.9% error), but the improvement in PWM prediction is dramatic (SKLD of 1.699 vs. 1.960), larger than the gain obtained in going from the Quasichemical to the DNAPROT algorithm (2.248 vs. 1.991), which accounts for intra-DNA interactions and requires consensus sequences. The positive impact of this second generalization on PWM prediction, but not on consensus sequence prediction, results, it is believed, because consensus sequences do not capture the relative binding strength of protein-DNA interactions for alternative DNA sequences.

Figure 5A:
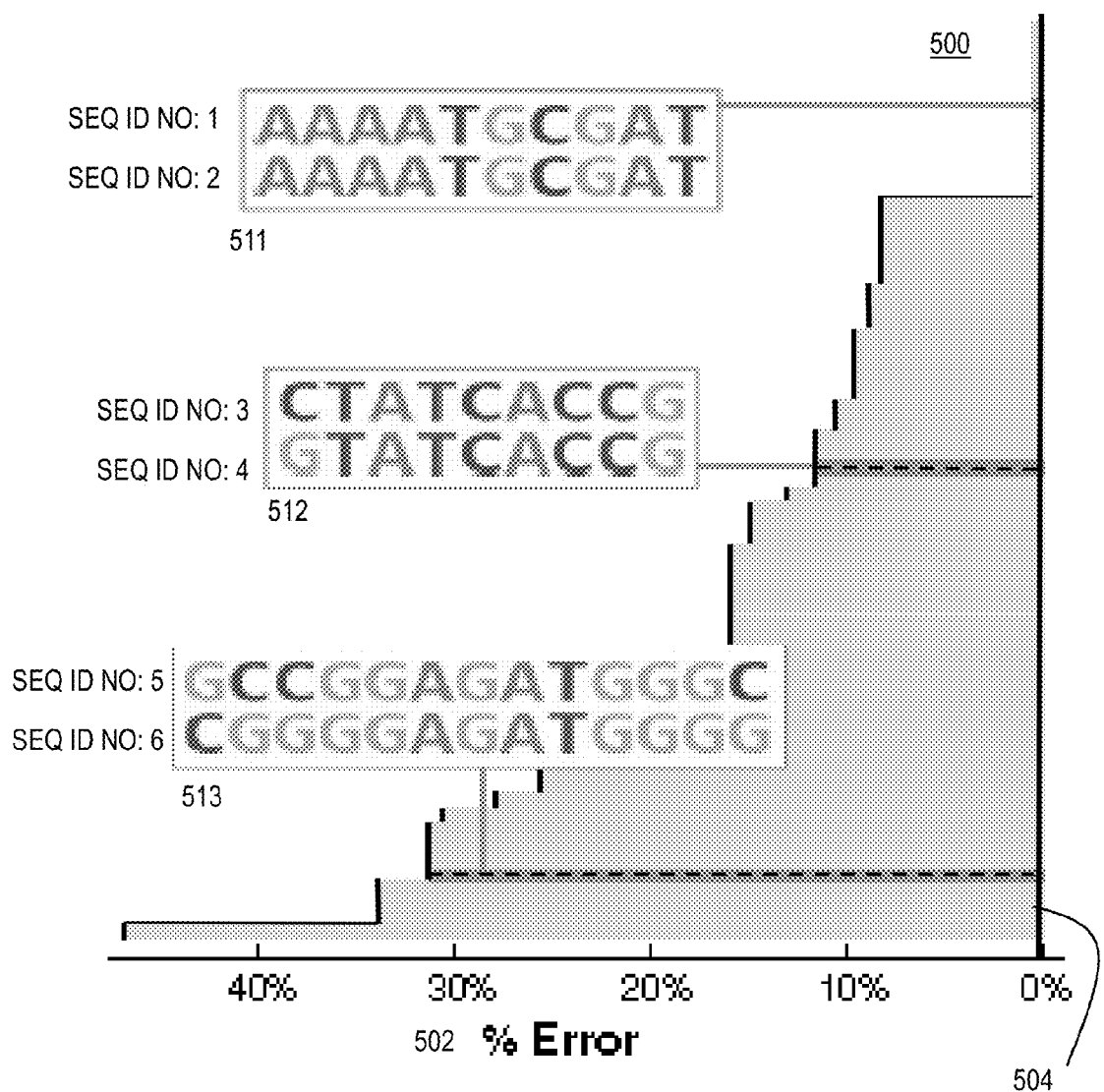
FIG. 5A (SEQ ID NOS: 1-6) and FIG. 5B (SEQ ID NOS: 7-13) are bar graphs that illustrates accuracy of predicted consensus sequences based on determined values of microscale interaction energy, according to an embodiment.
Figure 5B:
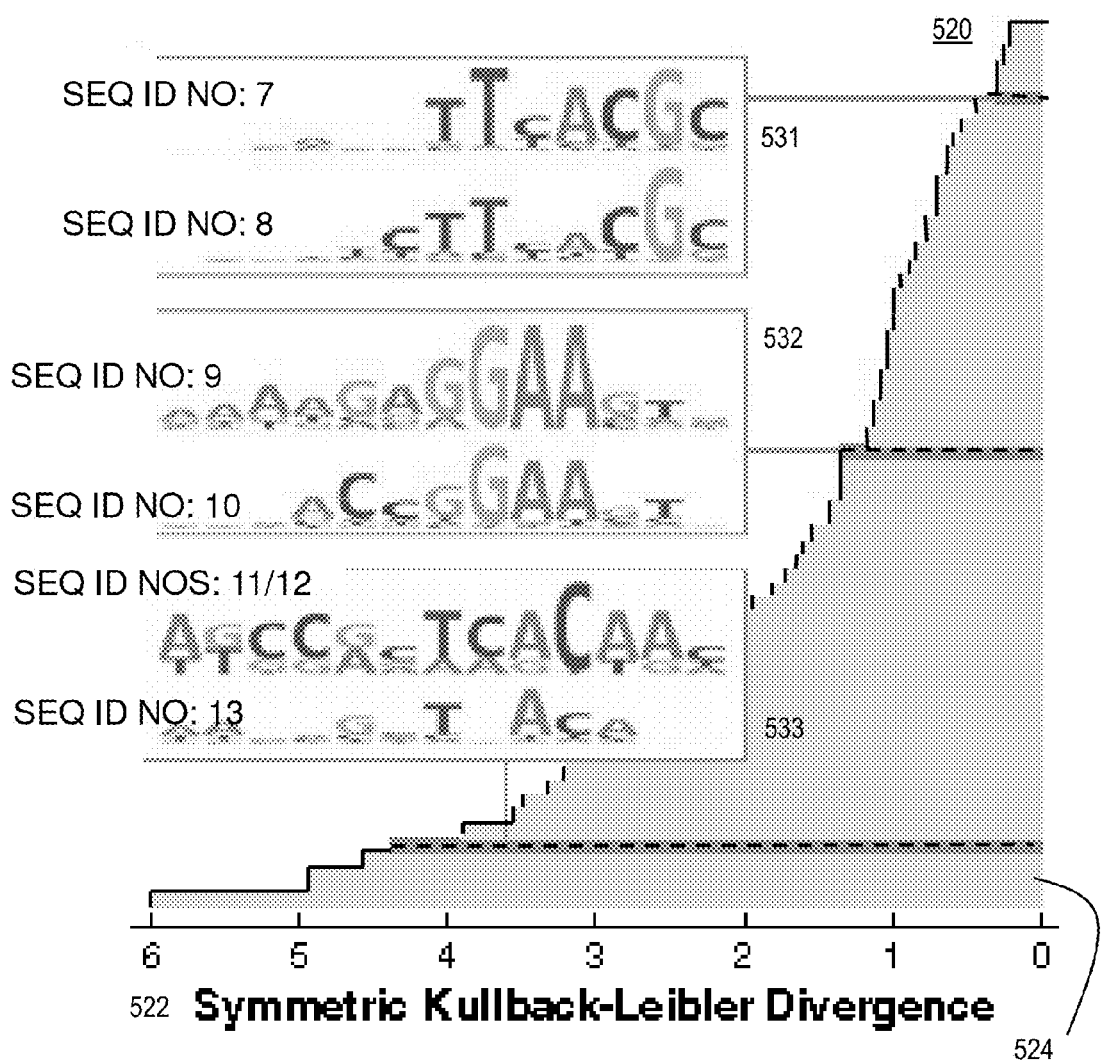

FIG. 5A and FIG. 5B are bar graphs that illustrates accuracy of predicted consensus sequences based on determined microscale energies, according to an embodiment. These graphs give representative performance of the de novo microscale potential in predicting DNA binding sites of 63 proteins. In FIG. 5A for bar graph 500, the horizontal axis 504 indicates the number of incorrect nucleotides (fraction of incorrect bases) in a predicted consensus sequence as a percentage error. The vertical axis indicates the 63 protein:DNA measurements in the data set for a combination of both generalizations. Each bar represents a combined prediction made by the algorithm, with shorter bars corresponding to better predictions. Highlighted examples (dashed lines) represent best, average, and worst cases, with insets 511 (SEQ ID NOS: 1-2), 512 (SEQ ID NOS: 3-4), 513 (SEQ ID NOS: 5-6) comparing experimentally-determined consensus sequence (top) to prediction (bottom) for representative best, average and worst predictions, respectively.

In FIG. 5B for bar graph 520, the horizontal axis 524 indicates difference of PWMs in SKLD dimensionless units. The vertical axis indicates the 63 protein:DNA measurements in the data set for both generalizations. Using SKLD scores for PWM predictions lower scores indicate better agreement, with insets 531 (SEQ ID NOS: 7-8), 532 (SEQ ID NOS: 9-10) and 533 (SEQ ID NOS: 11-13) comparing experimentally-determined PWM (top) to prediction (bottom) for representative best, average and worst predictions, respectively. Each PWM is represented by the letters indicating the 4 nucleotides (bases) at each position with a height that represents the probability of that nucleotide (base) at that position in a binding event between the protein and the DNA molecule.

Figure 6B:
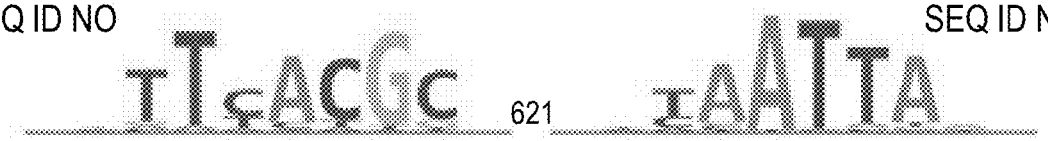
FIG. 6A (SEQ ID NOS: 14-23) and FIG. 6B (SEQ ID NOS: 24-30) are bar graphs that illustrate comparative predictions of consensus sequences, according to an embodiment.

FIG. 6A and FIG. 6B are diagrams that illustrates comparative prediction of consensus sequences, according to an embodiment. FIG. 6A and FIG. 6B compare predictions for the proteins where the illustrated de novo microscale potential embodiment exhibited the greatest improvements relative to other methods. These examples highlight significant improvement in prediction quality between de novo potential and other leading potentials. FIG. 6A shows experimental and predicted consensus sequences for the *D. melanogaster* Ultrabithorax Hox protein (left) and the *S. cerevisiae* MATa2 (right) protein. From top to bottom: line 601 (SEQ ID NOS: 14-15) shows experimental sequence, line 603 (SEQ ID NOS: 16-17) shows sequence based on de novo potential, line 605 (SEQ ID NOS: 18-19) shows sequence based on Rosetta (direct readout only), line 607 (SEQ ID NOS: 20-21) shows sequence based on Quasichemical, and line 609 (SEQ ID NOS: 22 shows sequence based on DNAPROT (direct readout only). FIG. 6B shows experimental and predicted PWMs for the *H. sapiens* Pax6 Paired domain (left) and *D. melanogaster* Engrailed homeodomain (right). From top to bottom: line 621 (SEQ ID NOS: 24-25) shows experimental PWM, line 623 (SEQ ID NOS: 26-27) shows PWM based on de novo potential of the present embodiment, line 625 shows PWM based on Rosetta, line 627 shows PWM based on Cumulative Contacts, line 629 (SEQ ID NOS: 28-29) shows PWM based on Quasichemical, and line 631 (SEQ ID NO: 30) shows PWM based on DNAPROT.

As discussed earlier, a collection of sensors must be substantively incoherent to insure high-quality reconstruction of the underlying potential with compressive sensing methods, and the potential must be sufficiently sparse relative to the number of available measurements. To determine the degree to which these requirements are satisfied by the potentials derived from the protein:DNA complexes in the illustrated embodiment, the best performing Baseline model was considered, applied without the two generalizations discussed in the previous section. This model produced values of potential for a total of 2,997 unique microscale interactions using 1.3 Å wide distance bins and 5.9 Å cutoff distance as metaparameters. The total number of sensors in the data set is 592, as each protein-DNA crystal structure yields multiple sensors (making the common assumption of independence between DNA basepair positions). As previously noted, accurate inference is still possible despite having a smaller number of sensors than the number of unique microscale interactions, if the potential is sufficiently sparse. Of the 2,997 unique interactions, only 270 have non-negligible values of potential, suggesting that the illustrated embodiment will yield accurate potentials. In fact, it is likely that the best performing choices of binning width and cutoff distance used for the Baseline model represent the optimal tradeoff between spatial resolution and statistical power.

The protein-DNA binding site predictions reported exhibit a dramatic improvement over the leading alternative methods, with predictions within the experimental error of the PWMs for at least half of the cases studied. Although the accuracy depicted in FIG. 5A and FIG. 5B is substantially better than achieved with alternative methods, the predictions for the proteins in the lower quarter of the figure should be improved. The 63 protein-DNA complexes in the illustrated database may provide biased or insufficient coverage of some of the microscale interactions. Or, there could be significant variance in the quality of the crystal structures determined for the different complexes in the database that we curated from the Protein Data Base. Additionally, prediction errors might reflect the effects of other mechanisms that affect the shape and accessibility of the DNA in vivo so that the structure of the crystallized complex differs from the in vivo structure. Also, some transcription factors have been observed to bind DNA with two or more distinct motifs, and the alternate motifs would be missing from the data set used.

As in other CS application domains, the accuracy of the inferred potentials depends on the characteristics of the sensor matrix; in this case, the collection of protein-DNA structures available. As discussed above, quantitative measures such as coherence can be used to assess the suitability of a sensor matrix for compressive sensing. These measures can provide a principled framework for selecting additional crystallization targets that will maximally enhance the sensing performance of a protein-DNA structural data set. It was shown above that the example data set has good incoherence properties, yet it is expected that the addition of more protein-DNA crystal structures, specifically chosen to yield a sensor matrix with even lower coherence, will yield more accurate potentials and better binding site predictions.

While statistical potentials and the illustrated embodiments both use experimental data sets to derive the final potential, de novo potentials of the illustrated embodiment are nonparametric, i.e. they do not assume an underlying mathematical form. In contrast, statistical potentials rely on experimental data sets to fit a parametric model with a fixed mathematical form. De novo potentials overcome additional limitations specific to statistical potentials. First, while statistical potentials only utilize atomic data such as crystal structures to fit their parameters, de novo potentials combine structural information and experimental binding data into a single formulation for inference. In the field of protein-DNA binding site prediction, combining these types of data has been a longstanding objective. Second, statistical potentials implicitly assume that all structures come from the same canonical ensemble. This oversimplification ignores the chain connectivity and amino acid composition of proteins, and it is thought to be the cause of common anomalies observed in statistical potentials. In de novo potentials, this assumption is eliminated in the energy-based formulation, and it is relaxed significantly in the probability-based formulation, so that only subsets of the data are assumed to form canonical ensembles. Third, by assigning equal weight to microscale interactions observed in different structures, statistical potentials implicitly assume that different structures have the same binding or formation energy. This is not the case, as different protein-DNA complexes are known to have different binding affinities. From a statistical mechanical standpoint, high affinity complexes correspond to more frequent mesoscale interactions than low affinity complexes, requiring that the underlying microscale interactions be given proportionally greater weight. De novo potentials take this into account, as the binding energies of mesoscale interactions are an explicit part of the formulation. Fourth, there is no theoretical assurance that as more data is added for the statistical potential fitting process, the inferred energies will ultimately converge to the true underlying interaction energies. The same observation holds for physical potentials. In contrast, for de novo potentials, if the formal requirements of compressed sensing are satisfied, then additional sensors in the data set will lead to ever closer estimates of the interaction energies.

The important insight that underlies the de novo methodology illustrated here is that experimental data sets relating to mesoscale interactions in a wide range of fields can be cast as incoherent measurements of microscale interactions in the compressed sensing framework. In these cases, powerful compressed sensing methods can be used to determine de novo potentials. In the current protein-DNA application, microscale interactions were defined to always involve one protein atom and one DNA atom, thus neglecting intra-DNA interactions. If microscale interactions are defined to include non-covalent contacts between two DNA atoms, then the indirect readout component of protein-DNA interactions can also be modeled, capturing intra-DNA interactions.

Similarly, to infer a potential for protein-protein interactions or for protein folding, non-covalent contacts between protein atoms would be treated as the microscale interactions. However, interactions need not be restricted to those involving pairs of atoms. Interactions involving multiple atoms, as well as coarse-grained potentials in which the "atoms" of the systems are residues for example, could be used. For mesoscale measurements of protein-protein interactions, biochemical data on protein-protein binding kinetics can be used. The Protein-protein Interaction Thermodynamic Database (PINT) is a database of such measurements (e.g., see Kumar M. D. and M. M. Gromiha, "PINT: Protein-protein Interactions Thermodynamic Database," *Nucleic Acids Res* v34, Database issue, pp D195-198, 2006). For mesoscale measurements of protein folding, the kinetics or mean folding times of proteins are used. While such measurements are difficult to obtain, significant progress in experimental techniques has been made recently. The advent of these new experimental techniques promises to make such measurements more readily available in the future.

4. Commercial Applications or Contexts

Signaling Networks.

The ability to predict protein binding sites on DNA and other biomolecular interaction kinetics will have profound practical benefits for accelerating and reducing the cost of determining cellular signaling networks. Defects in cell signaling are important in many diseases. This method will enable accurate computational prediction of effects of mutations in signaling proteins in their active regions or in DNA sequences within binding sites.

Drug Interaction Sites.

The quantitative microscale potentials yielded by this method will enable drug designers to predict drug interaction sites and drug reactivity with greater precision than now possible.

Bioreactors.

Molecular binding affinities are an important determinant of enzyme reaction rates. Knowledge of the microscale potentials that are the basis for these binding affinities will enable design of custom enzymes for application in commercial bioreactors, including those involved in production of biofuels.

Gene Regulatory Networks.

Understanding of genetic regulation in all organisms is dependent on identification of the genes regulated by each particular protein transcription factor. That is, determining the genes that have binding sites for each transcription factor. Currently, the laboratory procedures required for these identifications are complex, expensive, and labor intensive. The ability to computationally predict these binding sites, and hence the regulated genes, will enable much more focused, and hence less expensive, laboratory procedures. These benefits will accrue even for predictions that are not absolutely precise, by reducing the number of possibilities that have to be explored in the laboratory. These benefits are particularly important for human genetics, due to the complexity of the genetic regulation of higher organisms, and to the difficulty of doing laboratory experiments on mammalian subjects.

Gene Therapy.

A major challenge in the field of gene therapy is the design of enzymes that insert new genetic material into specific regions of the human genome. Without the ability to target these insertions with high accuracy, misplaced insertions can lead to significant side effects on the patient's health. The design of sequence-specific enzymes depends on our ability to predict the DNA-binding site of those enzymes, which is a major application of this method.

Molecular Dynamics Simulation.

Potentials are used as the basis of any molecular dynamics simulation, in the form of the energy function that is used to compute the energy of the simulated system at every step of the simulation. Consequently the accuracy of molecular dynamics simulations is intimately related to the accuracy of the underlying potential. This method provides a purely experiment-based approach to infer such potentials with higher accuracy than is now possible with conventional potentials.

5. Hardware Overview

Figure 7:
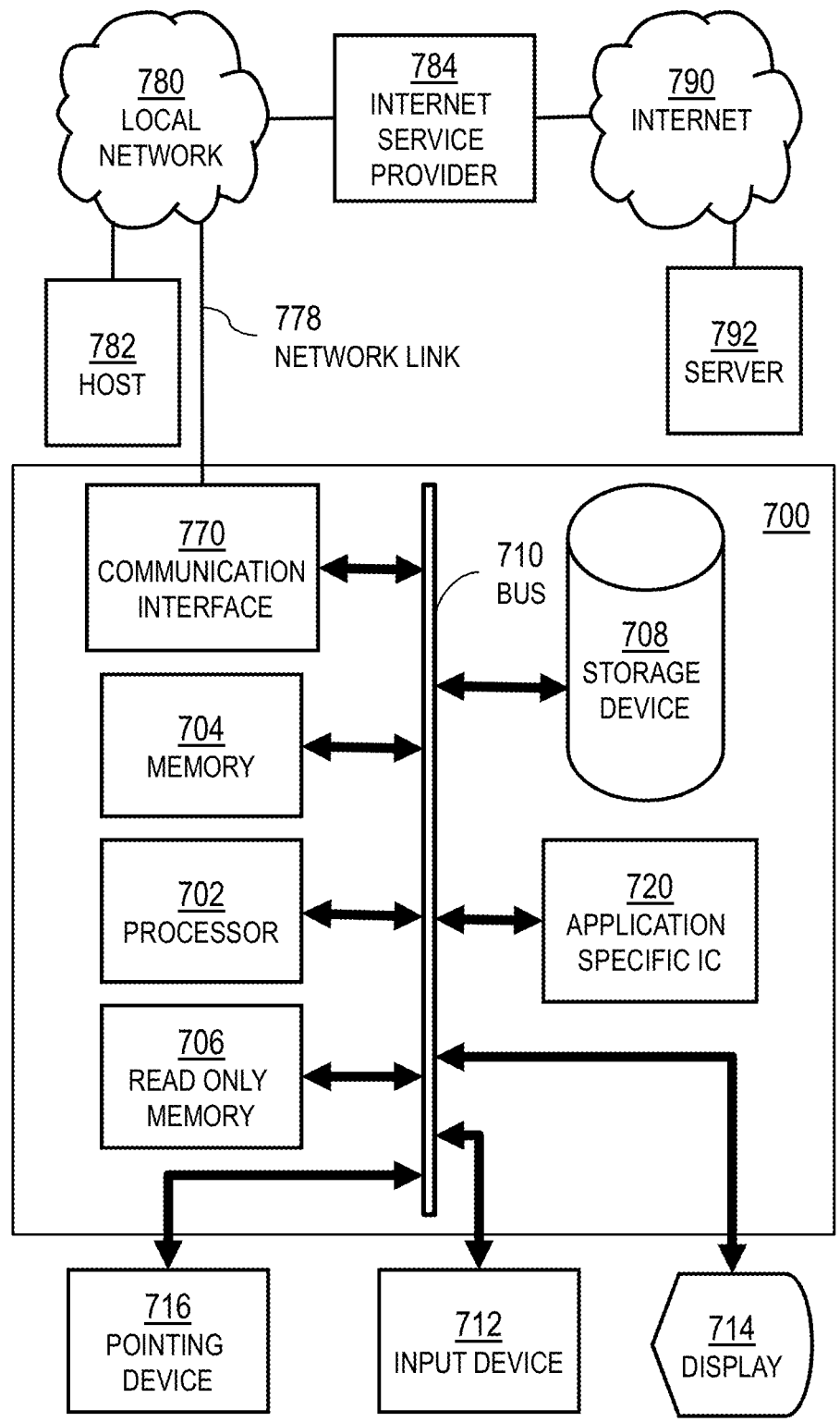
FIG. 7 is a block diagram that illustrates a computer system upon which an embodiment of the invention may be implemented.

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 700, or a portion thereof, constitutes a means for performing one or more steps of one or more methods described herein.

A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 702, except for carrier waves and other signals.

Logic encoded in one or more tangible media includes one or both of processor instructions on a computer-readable storage media and special purpose hardware, such as ASIC 720.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

FIG. 8 illustrates a chip set 800 upon which an embodiment of the invention may be implemented. Chip set 800 is programmed to perform one or more steps of a method described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 800, or a portion thereof, constitutes a means for performing one or more steps of a method described herein.

In one embodiment, the chip set 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound)

in real time independently of the processor 803. Similarly, an ASIC 809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 805 also stores the data associated with or generated by the execution of one or more steps of the methods described herein.

6. Alternatives and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
 determining a microscale metric for a plurality of microscale interaction types;
 determining a mesoscale metric for a plurality of mesoscale interaction types, wherein a value of the mesoscale metric for each mesoscale interaction type is based on a corresponding function of values of the microscale metric for the plurality of the microscale interaction types;
 obtaining a plurality of observations that indicate the values of the mesoscale metric for the plurality of mesoscale interaction types; and
 determining values of the microscale metric for the plurality of microscale interaction types based on the plurality of observations and the corresponding functions and compressed sensing.

2. A method as recited in claim 1, wherein the plurality of microscale interactions includes sub-molecular interactions involving a plurality of atoms or atom complexes.

3. A method as recited in claim 1, wherein the plurality of mesoscale interactions include molecular interactions involving at least one large molecule.

4. A method as recited in claim 1, wherein the plurality of mesoscale interactions include molecular interactions involving at least one biomolecule.

5. A method as recited in claim 1, further comprising determining a value for the mesoscale metric for a different mesoscale interaction type based on a different function of the values of the microscale metric for the plurality of microscale interaction types.

6. A method as recited in claim 1, further comprising determining for each mesoscale interaction type the corresponding function of values of the microscale metric for the plurality of the micro scale interaction types.

7. A method as recited in claim 6, wherein determining for each mesoscale interaction the corresponding function is based on measurements from a member of a group comprising x-ray crystallography, nuclear magnetic resonance, cryo-electron microscopy, and atomic force microscopy.

8. A method as recited in claim 1, wherein the plurality of observations are based on mesoscale interactions in a corresponding plurality of crystals.

9. A method as recited in claim 1, wherein the metric of each mesoscale interaction comprises a binding energy of the mesoscale interaction.

10. A method as recited in claim 1, wherein the plurality of observations comprises a relative rate of occurrence of the mesoscale interaction in a canonical ensemble.

11. A method as recited in claim 1, wherein the metric for the plurality of microscale interaction types comprises potential.

12. A method as recited in claim 11, wherein the metric for the plurality of mesoscale interactions comprises binding energy.

13. A method as recited in claim 11, wherein the plurality of observations comprises relative rate of occurrence of the mesoscale interactions in a canonical ensemble.

14. A method as recited in claim 8, wherein each crystal comprises a plurality of occurrences of one protein molecule binding with one DNA molecule.

15. A method as recited in claim 1, wherein values for the microscale metric are negligible for a majority of the plurality of microscale interaction types.

* * * * *